United States Patent
Murdoch et al.

(10) Patent No.: US 10,209,208 B2
(45) Date of Patent: Feb. 19, 2019

(54) STABLE NANOCRYSTALLINE ORDERING ALLOY SYSTEMS AND METHODS OF IDENTIFYING SAME

(71) Applicant: Massachusetts Institute of Technology, Cambridge, MA (US)

(72) Inventors: Heather A. Murdoch, Baltimore, MD (US); Christopher A. Schuh, Wayland, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/659,515

(22) Filed: Jul. 25, 2017

(65) Prior Publication Data

US 2018/0100817 A1  Apr. 12, 2018

Related U.S. Application Data

(63) Continuation of application No. 14/282,691, filed on May 20, 2014, now Pat. No. 9,791,394.
(Continued)

(51) Int. Cl.
*G01N 25/00* (2006.01)
*G01N 25/02* (2006.01)
(Continued)

(52) U.S. Cl.
CPC ............ *G01N 25/02* (2013.01); *C22C 1/002* (2013.01); *C22C 5/02* (2013.01); *C22C 5/04* (2013.01);
(Continued)

(58) Field of Classification Search
USPC ........................................... 374/45, 100, 31
See application file for complete search history.

(56) References Cited

U.S. PATENT DOCUMENTS

| 5,425,822 A | 6/1995 | Hidaka et al. |
| 7,292,958 B2 | 11/2007 | Ceder et al. |

(Continued)

FOREIGN PATENT DOCUMENTS

| CN | 1958839 A | 5/2007 |
| CN | 101423912 A | 5/2009 |

(Continued)

OTHER PUBLICATIONS

U.S. Appl. No. 14/384,518, filed Sep. 14, 2011, Murdoch et al.
(Continued)

*Primary Examiner* — Mirellys Jagan
(74) *Attorney, Agent, or Firm* — Wolf, Greenfield & Sacks, P.C.

(57) ABSTRACT

Provided in one embodiment is a method of identifying a stable phase of an ordering binary alloy system comprising a solute element and a solvent element, the method comprising: determining at least three thermodynamic parameters associated with grain boundary segregation, phase separation, and intermetallic compound formation of the ordering binary alloy system; and identifying the stable phase of the ordering binary alloy system based on the first thermodynamic parameter, the second thermodynamic parameter and the third thermodynamic parameter by comparing the first thermodynamic parameter, the second thermodynamic parameter and the third thermodynamic parameter with a predetermined set of respective thermodynamic parameters to identify the stable phase; wherein the stable phase is one of a stable nanocrystalline phase, a metastable nanocrystalline phase, and a non-nanocrystalline phase.

15 Claims, 19 Drawing Sheets

Related U.S. Application Data

(60) Provisional application No. 61/825,675, filed on May 21, 2013.

(51) Int. Cl.

| | | |
|---|---|---|
| *C22C 5/02* | (2006.01) | |
| *C22C 5/04* | (2006.01) | |
| *C22C 5/06* | (2006.01) | |
| *C22C 9/00* | (2006.01) | |
| *C22C 11/00* | (2006.01) | |
| *C22C 12/00* | (2006.01) | |
| *C22C 13/00* | (2006.01) | |
| *C22C 14/00* | (2006.01) | |
| *C22C 16/00* | (2006.01) | |
| *C22C 18/00* | (2006.01) | |
| *C22C 19/03* | (2006.01) | |
| *C22C 19/07* | (2006.01) | |
| *C22C 20/00* | (2006.01) | |
| *C22C 24/00* | (2006.01) | |
| *C22C 27/00* | (2006.01) | |
| *C22C 27/02* | (2006.01) | |
| *C22C 27/04* | (2006.01) | |
| *C22C 28/00* | (2006.01) | |
| *C22C 38/06* | (2006.01) | |
| *C22C 1/00* | (2006.01) | |
| *C22C 45/00* | (2006.01) | |

(52) U.S. Cl.
CPC .............. *C22C 5/06* (2013.01); *C22C 9/00* (2013.01); *C22C 11/00* (2013.01); *C22C 12/00* (2013.01); *C22C 13/00* (2013.01); *C22C 14/00* (2013.01); *C22C 16/00* (2013.01); *C22C 18/00* (2013.01); *C22C 19/03* (2013.01); *C22C 19/07* (2013.01); *C22C 20/00* (2013.01); *C22C 24/00* (2013.01); *C22C 27/00* (2013.01); *C22C 27/02* (2013.01); *C22C 27/04* (2013.01); *C22C 28/00* (2013.01); *C22C 38/06* (2013.01); *C22C 45/00* (2013.01)

(56) References Cited

U.S. PATENT DOCUMENTS

| | | | |
|---|---|---|---|
| 7,520,944 | B2 | 4/2009 | Johnson |
| 9,791,394 | B2 | 10/2017 | Murdoch et al. |
| 2003/0041801 | A1 | 3/2003 | Hehmann |
| 2003/0183306 | A1 | 10/2003 | Hehmann et al. |
| 2006/0074594 | A1 | 4/2006 | Ceder et al. |
| 2006/0153728 | A1 | 7/2006 | Schoenung et al. |
| 2006/0191611 | A1 | 8/2006 | Johnson |
| 2007/0276638 | A1 | 11/2007 | Borchers et al. |
| 2010/0278682 | A1 | 11/2010 | Sasaki et al. |
| 2011/0277890 | A1 | 11/2011 | Bledsoe et al. |
| 2012/0232858 | A1 | 9/2012 | Zhou et al. |
| 2012/0270737 | A1 | 10/2012 | Sutter et al. |
| 2013/0133793 | A1* | 5/2013 | McDevitt ............ C22C 19/055 148/707 |
| 2014/0026776 | A1* | 1/2014 | Kecskes .................. B22F 3/02 102/305 |
| 2014/0276638 | A1* | 9/2014 | Steen .................. A61M 3/0241 604/521 |
| 2014/0283963 | A1 | 9/2014 | Gao et al. |
| 2014/0348203 | A1 | 11/2014 | Murdoch et al. |
| 2015/0125338 | A1 | 5/2015 | Murdoch et al. |
| 2015/0375301 | A1 | 12/2015 | Darling et al. |

FOREIGN PATENT DOCUMENTS

| | | |
|---|---|---|
| WO | WO 2005/005675 A2 | 1/2005 |
| WO | WO 2013/137857 A2 | 9/2013 |

OTHER PUBLICATIONS

PCT/US2014/038781, dated Sep. 4, 2014, **Invitation to Pay Additional Fees.
PCT/US2014/038781, dated Nov. 18, 2014, **International Search Report and Written Opinion.
201480029395.6, dated Jul. 22, 2016, **Chinese Office Action with English Translation.
201480029395.6, dated Mar. 3, 2017, **Chinese Office Action with English Translation.
201480029395.6, dated Sep. 13, 2017, Chinese Office Action with English Translation.
14801372.5, dated Dec. 21, 2016, **Extended European Search Report.
PCT/US2012/028811, dated Jul. 6, 2012, **International Search Report and Written Opinion.
PCT/US2012/028811, dated Sep. 25, 2015, **International Preliminary Report on Patentability.
**Office Communication dated Oct. 7, 2016 for U.S. Appl. No. 14/384,518.
**Office Communication dated Mar. 3, 2017 for U.S. Appl. No. 14/384,518.
**Office Communication dated Aug. 24, 2017 for U.S. Appl. No. 14/384,518.
Chinese Office Action dated Feb. 24, 2018 for Application No. 201611044120.7.
Office Communication for U.S. Appl. No. 14/384,518 dated Mar. 8, 2018.
Campbell, Thermodynamics and phase diagrams, Ch 3, in Phase Diagrams-Understanding the Basics. Mar. 2012, ASM International, www.asminternational.org, pp. 41-72.
Chookajorn et al., Design of stable nanocrystalline alloys. Science. Aug. 23, 2012;337(6097):951-4. doi: 10.1126/science.1224737.
Darling et al., Stabilized nanocrystalline iron-based alloys: Guiding efforts in alloy selection. Mat Sci Eng A. 2011;528:4365-71. Epub Mar. 2, 2011.
Ma, Alloys created between immiscible elements. Prog Mater Sci. 2005;50:413-509.
Oda et al., Microstructure and sinterability of nano-crystal tungsten powders. J Japan Inst Metals and Mater. 2005;69(11):967-72. doi:10/2320/jinstmet.69.697.
Ogawa, Mechanical properties of hot compacting high nitrogen nanocrystalline austenite stainless steel powders mechanically alloyed, Discussion 52, Collection of papers of lectures by the Iron and Steel Inst of Japan, Materials and Processes, Japan, Mar. 1, 1999;12(1):CAMP-ISIJ, ISSN:0914-6628.
Telu et al. Densification and characterisation of W-Cr-Nb alloys prepared by sintering of mechanically alloyed nanocrystalline powders. Powder Metallurgy. Feb. 28, 2013; 56(1):83-88.
U.S. Appl. No. 61/604,924, filed Feb. 29, 2012, Darling et al.
Invitation to Pay Additional Fees dated Sep. 4, 2014 in Application No. PCT/US2014/038781.
International Search Report and Written Opinion dated Nov. 18, 2014 for Application No. PCT/US2014/038781.
Chinese Office Action dated Jul. 22, 2016 for Application No. 201480029395.6.
Chinese Office Action dated Mar. 3, 2017 for Application No. 201480029395.6.
Chinese Office Action dated Sep. 13, 2017 for Application No. 201480029395.6.
Extended European Search Report dated Dec. 21, 2016 in Application No. 14801372.5.
International Search Report and Written Opinion dated Jul. 6, 2012 issued in connection with International Application No. PCT/US2012/028811.
International Preliminary Report on Patentability dated Sep. 25, 2014 in Application No. PCT/US2012/028811.
Office Communication for U.S. Appl. No. 14/384,518 dated Oct. 7, 2016.
Office Communication for U.S. Appl. No. 14/384,518 dated Mar. 9, 2017.
Office Communication for U.S. Appl. No. 14/384,518 dated Aug. 24, 2017.

(56) References Cited

OTHER PUBLICATIONS

Binder et al, "Computer Experiments on Phase Separation in Binary Alloys", Advances in Colloid and Interface Science, vol. 10, 99 173-214, 1979.

Bryden et al., Thermal stability and hydrogen absorption characteristics of palladium-yttrium nanoalloys. Acta Materialia 1996, 44(9): 3847-3854.

Chen et al., "Phase-Field Models for Microstructure Evolution," Annual Review of Materials Research, vol. 32, pp. 113-140. Aug. 2002.

Darling et al., Conference Presentation entitled "Grain Size Stabilization in Nanocrystalline Cu Alloys" given at the Minerals, Metals & Materials Society (TMS) 2011 Annual Conference, San Diego, CA, Mar. 1, 2011.

Eckert et al., "Thermal Stability and Grain Growth Behavior of Mechanically Alloyed Nanocrystalline FeCu Alloys," Journal of Applied Physics, vol. 73, pp. 131-141, Jan. 1993.

Koch et al., Stabilization of nanocrystalline grain sizes by solute additions. Journal of Material Science Dec. 2008, 43(23): 7264-7272.

Murdoch et al., Stability of binary nanocrystalline alloys against grain growth and phase separation. Acta Materialia Apr. 2013, 61(6): 2121-2132.

Saber et al., A predictive model for thermodynamic stability of grain size in nanocrystalline ternary alloys, J. Appl. Phys. 2013; 114(10): 103510.

Trelewicz et al., Grain boundary segregation and thermodynamically stable binary nanocrystalline alloys, Physical Review B. 2009; 79(9): 1-13.

Chinese Office Action dated Dec. 4, 2018 for Chinese Patent Application No. 201611044120.7.

Fan et al., Metallurgical and Materials Thermodynamics, Beijing: Metallurgical Industry Press, Jul. 2012, pp. 334-336.

\* cited by examiner

US 10,209,208 B2

STABLE NANOCRYSTALLINE ORDERING ALLOY SYSTEMS AND METHODS OF IDENTIFYING SAME

CROSS-REFERENCE TO RELATED PATENT APPLICATIONS

This application is a continuation of U.S. patent application Ser. No. 14/282,691 filed on May 20, 2014, which claims the benefit of and priority to U.S. Provisional Patent Application No. 61/825,675 filed on May 21, 2013, each of which is incorporated herein by reference in its entirety for all purposes.

STATEMENT REGARDING FEDERALLY SPONSORED RESEARCH

This invention was made with Government support under Grant No. W911NF-09-1-0422 and W911NF-07-D-0004 awarded by the Army Research Office. The Government has certain rights in the invention.

BACKGROUND

Pure nanocrystalline metals generally lack structural stability due to the energy associated with their high volume fraction of grain boundaries, often exhibiting grain growth even at room temperature. However, the addition of solute atoms can stabilize the nanostructure against grain growth. The mechanism for this improvement in stability has been proposed to involve the reduction of grain boundary energy through the segregation of solute atoms to the grain boundaries, with possible secondary kinetic contributions based on solute drag. Accordingly, alloying has emerged as an important component for the development and deployment of nanocrystalline materials, although basic understanding of stability in nanocrystalline alloys remains incomplete.

A number of models pertaining to grain boundary segregation in nanocrystalline systems have been developed. Starting from the Gibbs adsorption equation, Weissmuller noted that the segregation of solute atoms to the grain boundaries in a dilute system reduces the grain boundary energy, $\gamma$:

$$\gamma = \gamma_0 - \Gamma(\Delta H_{seg} + kT \log [X]) \quad (1)$$

where the reduction in grain boundary energy from the unalloyed condition, $\gamma_o$, is a function of the heat of segregation for the binary system ($\Delta H_{seg}$) and the solute excess ($\Gamma$) at the grain boundary for a particular global solute concentration (X) and temperature (T), with k the Boltzmann constant.

While the grain size-solute content relationships it predicted were promising with respect to experimental evidence, the stability of nanocrystalline systems was evaluated only with respect to changes in grain size. In fact, many of the analytical models to date suffer this deficiency. Suppression of grain growth is an important criterion for stabilizing a nanostructured alloy, but a potentially equally important stability is that with respect to phase separation. Even if a nanocrystalline alloy with grain boundary segregation is relatively more stable than a coarse-grained alloy of the same composition, the nanocrystalline state may never be achievable if the system phase separates.

Phase separation may be especially problematic in systems that may form intermetallic compounds. The formation of intermetallic compounds may provide an additional avenue for phase separation of the system, and may prevent the achievement of stable nanocrystalline alloy systems.

SUMMARY

In view of the foregoing, the Inventors have recognized and appreciated the advantages of the capability of predicting stable binary nanocrystalline alloy systems including having an ordering binary alloy system in a stable nanocrystalline phase against both grain growth and phase separation.

Accordingly, provided in one embodiment is a method of identifying a stable phase of an ordering binary alloy system comprising a solute element and a solvent element, the method comprising determining at least three thermodynamic parameters associated with grain boundary segregation, phase separation, and intermetallic compound formation of the ordering binary alloy system; and identifying the stable phase of the ordering binary alloy system based on the first thermodynamic parameter, the second thermodynamic parameter, and the third thermodynamic parameter by comparing the first thermodynamic parameter, the second thermodynamic parameter, and the third thermodynamic parameter with a predetermined set of respective thermodynamic parameters to identify the stable phase. The stable phase may be one of a stable nanocrystalline phase, a metastable nanocrystalline phase, and a non-nanocrystalline phase.

Provided in another embodiment is an article, comprising: a diagram delineating a plurality of regions respectively representing different stable phases of at least one ordering binary alloy system. The different stable phases of the at least one ordering binary alloy system may include at least one of a stable nanocrystalline phase, a metastable nanocrystalline phase, and a non-nanocrystalline phase. The respective regions of the plurality of regions may be delineated by at least one boundary determined as a function of the at least three thermodynamic parameters associated with grain boundary segregation, phase separation, and intermetallic compound formation of the at least one ordering binary alloy system.

Provided in another embodiment is a method of identifying a stable phase of an ordering binary alloy system comprising a solute element and a solvent element, the method comprising: determining at least three thermodynamic parameters associated with grain boundary segregation, phase separation, and formation of an intermetallic compound of the ordering binary alloy system; comparing the at least three thermodynamic parameters with a diagram delineating a plurality of regions respectively representing predetermined different stable phases of at least one predetermined ordering binary alloy system; and identifying the stable phase of the binary alloy based on the comparison. The predetermined different stable phases of the at least one predetermined ordering binary alloy system may include at least one of a stable nanocrystalline phase, a metastable nanocrystalline phase, and a non-nanocrystalline phase. The respective regions of the plurality of regions may be delineated by at least one boundary determined as a function of at least three thermodynamic parameters associated with grain growth, phase separation, and formation of an intermetallic compound of the at least one predetermined ordering binary alloy system.

Provided in another embodiment is a composition, comprising a nanocrystalline ordering binary alloy system with a negative heat of mixing. The ordering binary alloy system may be stable against grain growth and phase separation at a predetermined temperature.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The patent or application file contains at least one drawing executed in color. Copies of this patent or patent application publication with color drawings will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figures 1A, 1B:
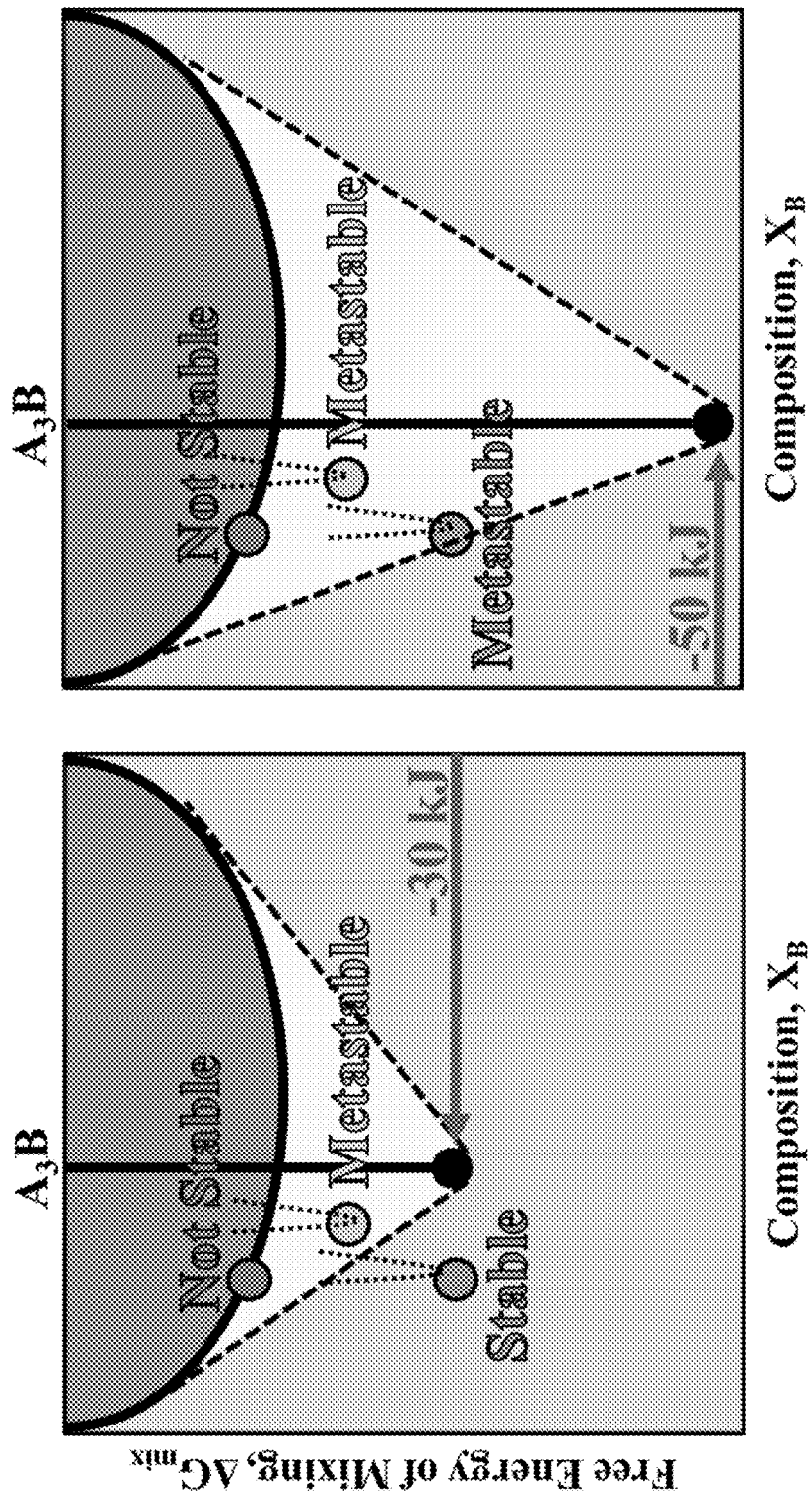
FIGS. 1A-1B show two exemplary free energy plots for stability conditions according to one embodiment for an ordering alloy system containing an $A_3B$ compound with a free energy of −30 kJ/mol and −50 kJ/mol, respectively. Green region: stable nanocrystalline (NC) microstructure; yellow region: metastable NC microstructure; red region: no stable NC microstructure.

Following below are more detailed descriptions of various concepts related to, and embodiments of, inventive stable nanocrystalline binary alloy systems and methods of predicting the same. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Stable Phase Nanocrystalline Ordering Alloy System

Provided in one embodiment are methods and articles that may be employed to identify the conditions under which nanocrystalline ordering binary alloy systems are stable with respect to both grain growth (e.g., segregation reduces the grain boundary energy to zero) and phase separation (e.g., the free energy of the nanocrystalline system is lower than the energy of formation of a secondary phase). The ordering binary alloy system may have a negative heat of mixing. In another embodiment, a "nanocrystalline stability map" is calculated at least with respect to ordering binary alloy system thermodynamic parameters. In one embodiment, at least three main regions may be delineated in these maps: one where grain boundary segregation does not result in a stabilized nanocrystalline structure, one in which phase separation would be preferential (despite the presence of a nanocrystalline state stable against grain growth), and one for which the nanocrystalline state is stable against both grain growth and phase separation. Additional details about the stabilized structures may also be included in the maps, which may be regarded as tools for the design of stable nanocrystalline ordering alloy systems.

One embodiment described herein is related to a method of identifying a stable phase of an ordering alloy system; the stable phase may be one of a stable nanocrystalline phase, a metastable nanocrystalline phase, and a non-nanocrystalline phase. Each of these phases are described in detail below.

The term "nanocrystalline" in at least some embodiments herein refers to the size of a crystal (or a "grain") being less than or equal to about 1000 nm—e.g., 500 nm, 200 nm, 100 nm, 50 nm, 20 nm, 10 nm, 5 nm, 2 nm, or less. For example, the grain size may be between 1000 nm and about 2 nm—e.g., about 500 nm and about 2 nm, about 200 nm and about 2 nm, about 100 nm and about 2 nm, about 50 nm and about 2 nm, about 30 nm and about 2 nm, about 20 and about 2 nm, about 10 nm and about 2 nm. In some embodiments, the size may refer to the largest dimension of the grain. The size of the grains referred to herein may be determined as an "average" and may be measured by any suitable techniques. The dimensions may refer to the diameter, length, width, and/or height, depending on the geometry of the grain. In some instances (and as provided below), a nanocrystalline material may also refer to a material comprising an amorphous microstructure.

The determination of the stable phase may involve the determination of a plurality of thermodynamic parameters. In some embodiments, the determination involves the determination of at least three thermodynamic parameters—e.g., four, five, or more. Each of the thermodynamic parameters may be associated with one or more phenomena (e.g., a physical phenomenon) related to the alloy system. For example, the at least three thermodynamic parameters may be associated with grain boundary segregation, phase separation, and intermetallic compound formation of the ordering binary alloy system. As described further below, based upon the thermodynamic parameters, the article, systems, and methods provided herein may be employed to identify the stable phase of an alloy system. The ordering alloy system may be a binary ordering alloy system (as described further below).

The term "stable phase" in at least some embodiments herein of an ordering alloy system refers to a phase of the alloy system that is present because it is favored energetically based on thermodynamics. In some embodiments, the stable phase occurs when the thermodynamic parameter(s) (e.g., free energy of mixing, enthalpy of mixing, enthalpy of segregation, free energy of formation of an intermetallic compound, etc.) associated therewith is at a minimum. Other thermodynamic parameters may also be employed. Depending on the parameters selected, they may be affected by other variables. For example, a thermodynamic parameter may comprise, or be, a free energy of mixing, which may be a function of at least one of (i) concentration of grain boundary in the binary alloy system, (ii) grain size of the binary alloy system, (iii) concentration of the solute element in the binary alloy system, and (iv) concentration of the solvent element in the binary alloy system.

Accordingly, when the ordering alloy system is stable (thermodynamically) as a stable nanocrystalline phase, the alloy will take the form of a nanocrystalline ordering alloy system. Alternatively, when the ordering alloy system is stable as a metastable nanocrystalline phase, as will be described below, competing driving forces take place: while one thermodynamic parameter of the ordering alloy system favors a nanocrystalline phase, another parameter favors phase separation (and thus no nanocrystalline phase). Thus, the ordering alloy system is metastable and any stimulus that may cause an energy fluctuation may drive the ordering alloy system towards a non-nanocrystalline phase. In another embodiment, when the ordering alloy system is stable as a non-nanocrystalline phase, the ordering alloy system may take the form of a non-nanocrystalline ordering alloy system, as the non-nanocrystalline phase is the phase energetically favored by thermodynamics.

Ordering Alloy Systems

Ordering alloy systems in at least some embodiments herein refer to alloy systems in which an intermetallic compound may be formed. An ordering alloy system may have a negative enthalpy of mixing (or "heat of mixing"). An ordering alloy system may include a stable nanocrystalline phase, a metastable nanocrystalline phase, or a non-nanocrystalline phase, in addition to an ordered intermetallic compound. Ordering alloy systems are distinct from alloy systems in which intermetallic compounds cannot be formed, such as alloy systems with positive enthalpies of mixing.

In one embodiment, to determine the stability of a nanocrystalline phase in an ordering alloy system against the formation of secondary phases, the free energy of the nanocrystalline phase is compared to the free energy of other possible phases. In one embodiment, the other possible phases may include a solid solution and the ordered intermetallic compounds.

The ordering alloy system described in at least some embodiments herein may be a binary alloy system, ternary alloy system, or an alloy system with a higher number of constituents. In some embodiments, an ordering binary alloy system may contain a solute element (or solute atoms) and a solvent element (or solvent atoms). While the main constituents of an ordering binary alloy system are the solute and the solvent elements, some incidental minute trace amount of impurity element(s) may also be present. The designation of a solute versus a solvent element need not be rigid. In general, the constituent element in the system that has the higher amount may be considered as the solvent element, while the other that has the lower amount may be considered as the solute element.

In some embodiments, the range of compositions over which the desired nanocrystalline stable structure is obtained may be different. For example, it may occur at an alloy solute content of at least about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%. In some embodiments, the solute content may range from about 0.1% to about 48%—e.g., about 0.5% to about 45%, about 1% to about 40%, about 2% to about 38%, about 3% to about 36%, about 5% to about 34%, about 6% to about 32%, about 8% to about 30%, about 10% to about 28%, about 12% to about 26%, about 14% to about 24%, about 16% to about 22%, about 18% to about 20%. In some other embodiments, the solute content may be in one of the following ranges: about 0.5% to about 1%, about 2% to about 4%, about 4% to about 6%, about 6% to about 8%, about 8% to about 10%, about 12% to about 14%, about 14% to about 16% about 16% to about 18%, and about 18% to about 20%. Higher or lower percentages than those provided herein are also possible, depending on the materials. The percentage herein may refer to either volume percentage or mass percent, depending on the context.

The intermetallic compounds in ordering alloy systems may be described by input parameters (as the phases) different from those employed in the Regular Nanocrystalline Solution (RNS) model, which is further described below. FIGS. 1A-18B, as described below, may be employed to facilitate the explanation of the model and the application thereof. For example, the free energy of the common $L1_0$ compound is defined in terms of both $\omega_c$, a collection of the energies of A-A, B-B, and A-B bonds, and the energies of pure A-A and B-B bonds. The RNS model includes no parameter analogous to bulk A-A and B-B bonds in the absence of A-B bonds or grain boundary bonds. Thus, the inputs of the RNS model do not include all of the parameters needed for determining the free energy of formation of an ordered intermetallic compound. The stabilities of the system in some embodiments are illustrated in FIGS. 8A-12D and described further below. Also, the free energy of formation of the ordered intermetallic compound may be considered in addition to the input parameters of the RNS model to determine the stability of the nanocrystalline phase. The stability maps of different systems are provided in FIGS. 1A-1B, 2A-2B, 13, and 14 for one type of (ordering) alloy system with a negative heat of mixing and in FIGS. 15-18B for another system with a positive heat of mixing.

The stability of the nanocrystalline phase may be determined by comparing the free energy of the nanocrystalline phase to an absolute value of free energy for a compound phase, without taking into account any specific structural considerations. In one embodiment, a comparison of this type allows numerous intermetallic compounds that may form at a given composition to be represented by the same stability metric.

The free energy of the intermetallic compound may determine whether a nanocrystalline phase is stable or metastable for a given set of parameters $(z, \omega_e)$. An intermetallic compound with any type of structure, depending on the specific alloy system, may be represented by a single metric on a stability map. The single metric may refer to a thermodynamic parameter. The parameter may be associated with the free energy of formation of the intermetallic compound. A nanocrystalline structure that is stable against a solid solution may be stable in an ordering alloy system comprising an $A_3B$ compound with a free energy of −30 kJ/mol, as depicted in FIG. 1A, while the same nanocrystalline structure is only metastable with an $A_3B$ compound with a free energy of −50 kJ/mol, as depicted in FIG. 1B. Generally, the region of metastability may increase as the free energy of the intermetallic compound decreases.

Figures 2A, 2B:
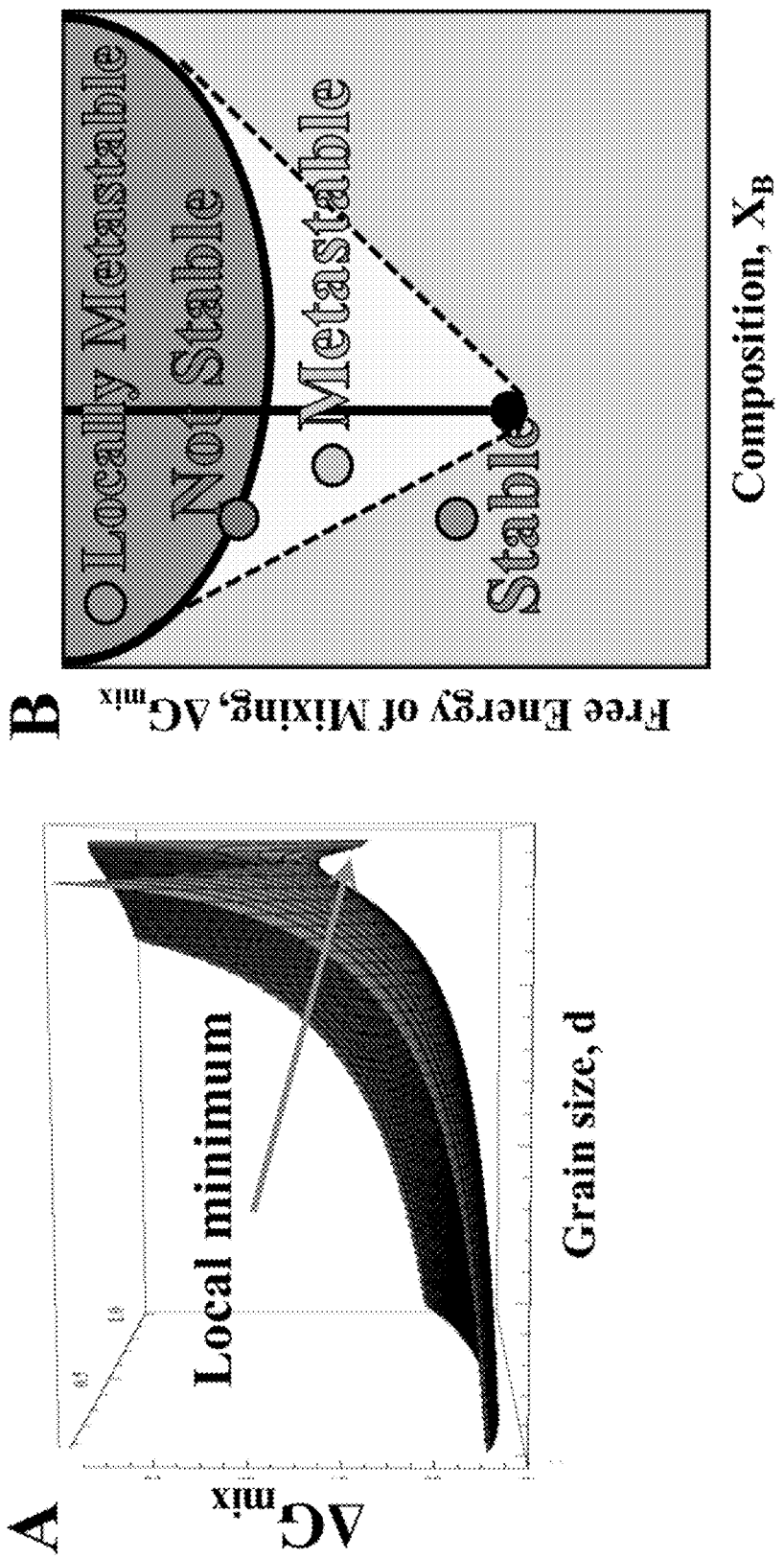
FIGS. 2A-2B show a free energy surface with a local minimum and a free energy plot depicting the location of the local minimum point relative to other phases, respectively, of an ordering alloy system with a negative enthalpy of mixing in one embodiment.

As depicted in FIG. 2B, four different possible stability states of a nanocrystalline phase may exist. The first state may refer to a situation where no free energy minimum exists, indicating that a nanocrystalline phase will not be stable—this is depicted in red in the figure. The second state may refer to the existence of a nanocrystalline phase local free energy minimum; the free energy of the solid solution or non-nanocrystalline structure at that composition may be lower than the local minimum of the nanocrystalline phase. This phase is considered to be locally metastable, and is depicted in orange in the figure. The third state may refer to a state where a nanocrystalline phase free energy minimum exists and is lower in free energy than the solid solution at the same composition. The free energy of an intermetallic compound in this state may share a common tangent (dashed lines) with the solid solution, demonstrating that the lowest energy phase combination is that of the intermetallic compound and the solid solution. The phases of this type are considered to be metastable, and are depicted in yellow in the figure. Lastly, the fourth state may refer to a state where a stable nanocrystalline phase exists when the free energy of the nanocrystalline phase is lower than all other possible phases, as depicted in green in the figure.

The ordering alloy system may have a negative enthalpy of mixing. In at least some embodiments, ordering alloy systems may not have a characteristic temperature that can be related to the other inputs of the RNS model in the manner that $T_{cr}$ may be for positive enthalpy of mixing systems. Thus, analysis of the stability of ordering alloy systems may be performed for an absolute temperature.

Modified Regular Nanocrystalline Solution (RNS) Model

A model by Trelewicz proposes a regular nanocrystalline solution (RNS) model for the free energy of mixing in binary alloys with both crystalline and intercrystalline atomic environments. The RNS model reduces to a regular solution model for the crystalline phase in the limit of infinite grain size and to a standard grain boundary segregation isotherm in the dilute limit. However, the model by Trelewicz, along with many of the other models to date, evaluates only changes in grain size. This type of evaluation suffers the deficiency of not being able to account for phase separation.

Accordingly, building upon the Trelewicz RNS model but in contrast thereto, the methods and articles described herein evaluate and predict ordering alloy systems based upon the thermodynamic parameters associated with not only grain growth but also phase separation. The Trelewicz RNS based portion of the model utilized by the presently described methods, systems, and articles according to one embodiment applies in a similar manner to alloy systems with a positive heat of mixing and ordering alloy systems with a negative heat of mixing, and is described as follows:

An intergranular region (ig) and a region in the grain interior (g) with the total solute concentration, X, are defined, satisfying the balance:

$$X = f_{ig}X_{ig} + (1-f_{ig})X_g, \qquad (2)$$

where $X_{ig}$ is the concentration of solute species in the intergranular region, $X_g$ is the concentration in the grains, and $f_{ig}$ is the volume fraction of the intergranular region:

$$f_{ig} = 1 - \left(\frac{d-t}{d}\right)^D, \quad (3)$$

where d is the grain diameter, t is the thickness of the grain boundary region (taken to be 0.5 nm in some embodiments but may be any other suitable values), and D is the dimensionality of the grain structure (taken to be D=3 in some embodiments but may be any other suitable values). The model herein also describes a transition region referring to the bonds between the atoms in the grain and in the intergranular region.

Figure 3:
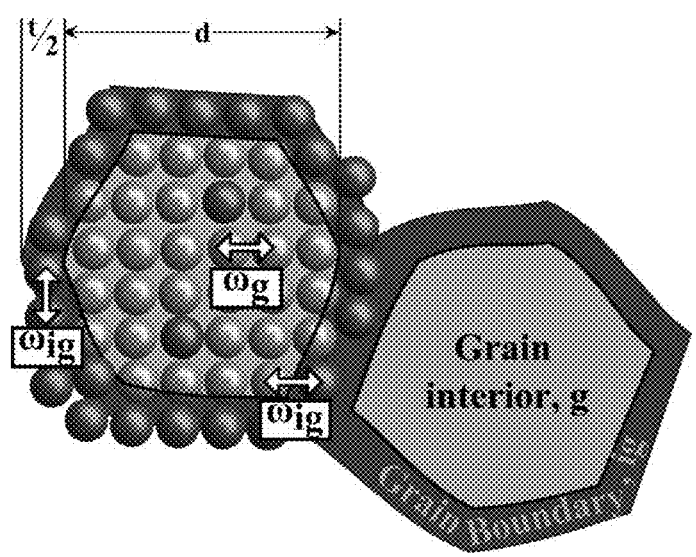
FIG. 3 provides a schematic of two nanocrystalline grains exhibiting grain boundary segregation in one embodiment; grey atoms represent solvent atoms and red atoms represent solute atoms.

The analytical developments of the RNS model are statistical and envision the system as a population of atoms and bonds as illustrated on the left of FIG. 3; FIG. 3 shows the interaction between a pair of atoms and the parameter describing their interaction in one embodiment. While the schematic on the left of FIG. 3 provides a view of discrete atoms, the system in general may be viewed as a continuum as shown on the right of FIG. 3. The spatial distribution of atomic bonds between the three regions, the energies associated with creating grain boundaries, and region-weighted entropic contributions may be encapsulated in the final free energy function derived from the model:

$$\Delta G_{mix} = (1 - f_{ig})\Delta G_{mix}^g + f_{ig}\Delta G_{mix}^{ig} + \quad (4)$$

$$zvf_{ig}(X_{ig} - X_g)\left[(2X_{ig} - 1)\omega_{ig} - \frac{1}{zt}(\Omega^B \gamma^B - \Omega^A \gamma^A)\right],$$

where z is the coordination number of the bulk material, $\Omega$ is the atomic volume, v is the transitional bond fraction (the fraction of atoms contributing bonds to the transitional bonding region), and $\omega$ is the interaction parameter defined as:

$$\omega = E^{AB} - \frac{E^{AA} + E^{BB}}{2}, \quad (5)$$

Two separate interaction parameters may be used to describe the binary nanocrystalline ordering alloy system: a bulk parameter $\omega_g$ describing the grain interior and $\omega_{ig}$ describing the interactions in the grain boundary and transition regions. This intergranular interaction may or may not differ in character from that in the bulk. A positive interaction parameter denotes a phase-separating system—i.e., where the energy of AB bonds is greater than the average energy of AA and BB bonds (A and B represent different types of atoms). The interaction parameter may be related to the heat of mixing via:

$$\Delta H_{mix} = z\omega_g X(1-X) \quad (6)$$

The terms $\Delta G_{mix}^g$ and $\Delta G_{mix}^{ig}$ represent the outer boundaries of the system according to one embodiment. As an illustration, if the material contains only grain interior ($d\to\infty$, $f_{ig}\to 0$), the free energy function reduces to that of a classical regular solution:

$$\Delta G_{mix}^g = z\omega_g X_g(1-X_g) + kT[X_g \ln X_g + [(1-X]_g)\ln(1-X_g)]. \quad (7)$$

On the other hand, at the lower limit (or boundary) of grain size (d=t) is the free energy term of the intergranular regular solution, which may include a dependence on the grain boundary energies of both grain and grain boundaries:

$$\Delta G_{mix}^{ig} = z\omega_{ig}X_{ig}(1 - X_{ig}) + \frac{\Omega}{t}(1 - X_{ig})\gamma_A + \quad (8)$$

$$\frac{\Omega}{t}X_{ig}\gamma_B kT[X_{ig}\ln X_{ig} + [((1 - X)]_{ig})\ln(1 - X_{ig})].$$

Figures 4A, 4B:
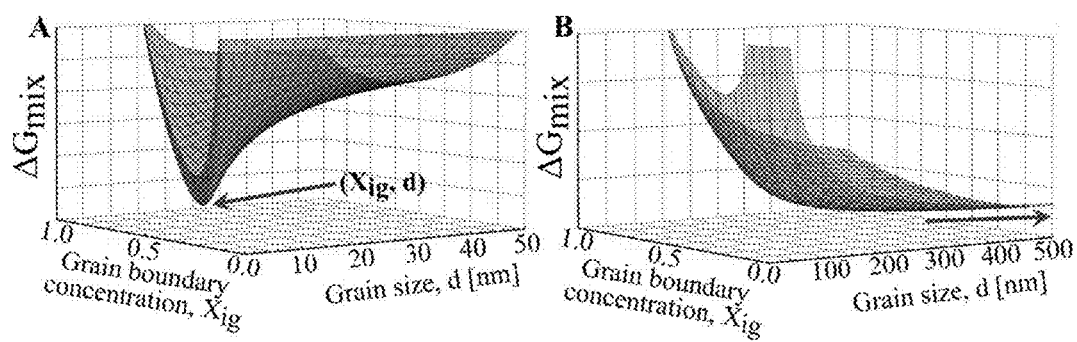
FIGS. 4A-4B show Gibbs free energy of a mixing surface for respectively a single value of global solute concentration and for no presence of nanocrystalline minimum.

The remaining terms in Eq. (4) describe the transition region. In some embodiments, the model described herein may be used to identify nanocrystalline alloys with segregation states that lead to formal stability against coarsening. Building upon the Trelewicz model, the model described herein also may generate a free-energy surface as shown in FIGS. 4A-4B, plotted as a function of grain size (d) and intergranular concentration ($X_{ig}$) at a constant global solute content and temperature. The minimum of the curve (shown larger in FIG. 5) represents a grain size and intergranular solute concentration at which the grain boundary energy for the given global solute concentration is zero. FIG. 4B shows a free energy surface with no nanocrystalline minimum present; the minimum value corresponds to that of the bulk regular solution (infinite grain size).

For certain combinations of input parameters (e.g., interaction parameters co, global concentration and temperature), the free-energy surface may exhibit a global minimum at a pair value of ($X_{ig}$, d), for which the nanocrystalline microstructure is stable. See FIG. 4A. The minimum on the concentration axis ($X_{ig}$) shows the segregation state that is neither over-full nor under-full (i.e., ideally saturated with solute). The minimum with respect to grain size corresponds to an alloy grain boundary energy of zero, and demonstrates a nanostructure that is stable with respect to grain growth. The existence of a minimum in the free energy surface depends on the materials' parameters and the solute content of the system. There may be cases where a nontrivial minimum does not exist (e.g., FIG. 4B), for which the "preferred" grain size is infinite, and the free energy of the system matches that of a bulk regular solution for the same global solute content.

As described above, the model herein accounts for not only grain growth, but also phase separation. In some embodiments, a comparison is performed for a given minimum-energy configuration of the kind as shown in FIG. 4A, which only considers segregated nanocrystalline solid solution configurations for a single composition, against other possible configurations that involve phase separation.

In some embodiments, the free energy surface constructed for a discrete value of global solute content (i.e., of the kind shown in FIG. 4A), with a minimum at a given value of grain boundary composition and grain size, ($X_{ig}$, d) is evaluated. The examination of the region of the minimum in such a surface in one embodiment is illustrated in FIG. 5, in which the values of $X_{ig}$ and d are held constant and the global composition, X, is varied.

Figure 5:
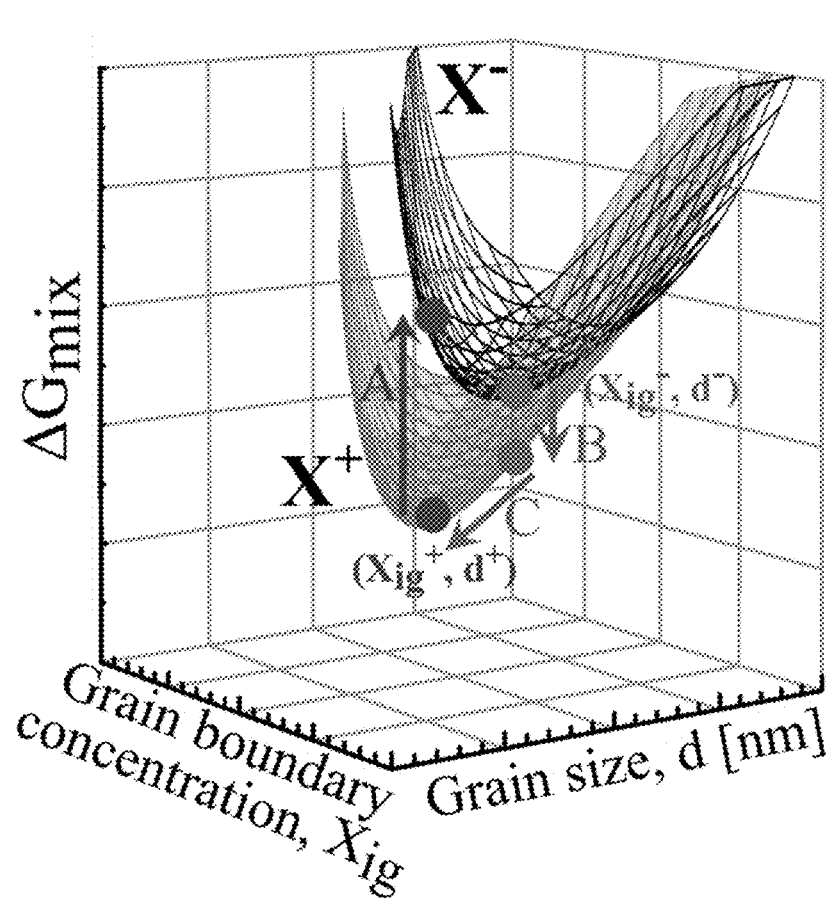
FIG. 5 shows minima in the free energy surface for two global solute concentrations, $X^+$ and $X^-$ in one embodiment. See FIGS. 6A-6B for an alternative presentation.

For the purposes of illustration in FIG. 5, consider two global compositions $X^+$ and $X^-$, slightly different from one another, to which two global compositions may be compared. At the global concentration $X^+$, a minimum occurs in the free energy surface (lower magenta curve in FIG. 5) at a specific value of intergranular concentration and grain size, ($X_{ig}^+$, $d^+$). If the global composition is decreased to $X^-$ for the values ($X_{ig}^+$, $d^+$), the free energy increases. In one embodiment, this increase may be rapid with respect to even small changes in global composition, as shown by the arrow A in FIG. 5; this is similar to the free energy behavior of a stoichiometric line compound phase, with a single preferred composition for which the energy is minimized. On the other hand, if we instead start with the global composition $X^-$, with the minimum at $(X_{ig}^-, d^-)$ and increase the composition (FIG. 5, arrow B), the grain boundary energy drops to less than zero, indicating that the grain size would prefer to decrease. On this new free energy surface for the higher composition $(X^+)$, the system can decrease its energy by obtaining a new minimum (FIG. 5, arrow C) at a smaller grain size.

Figure 6A:
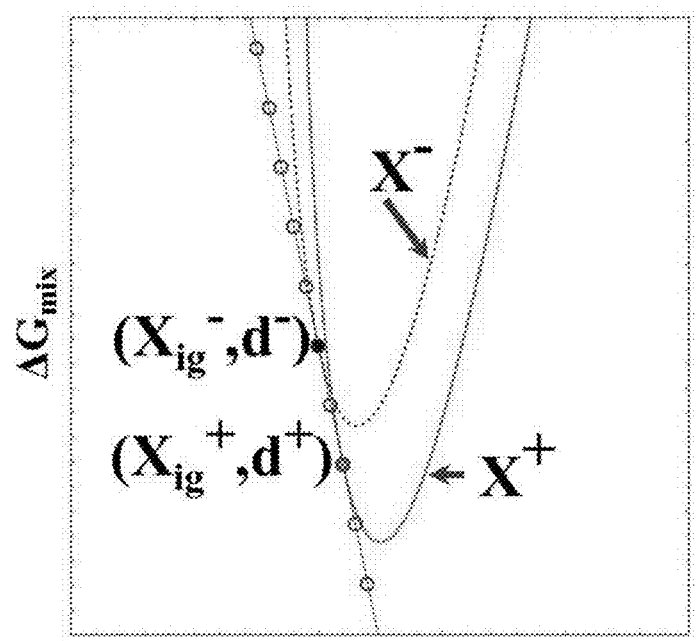
FIGS. 6A-6B illustrate relationships between free energy of mixing and grain boundary energy, respectively, as a function of global composition, X in one embodiment.
Figure 6B:
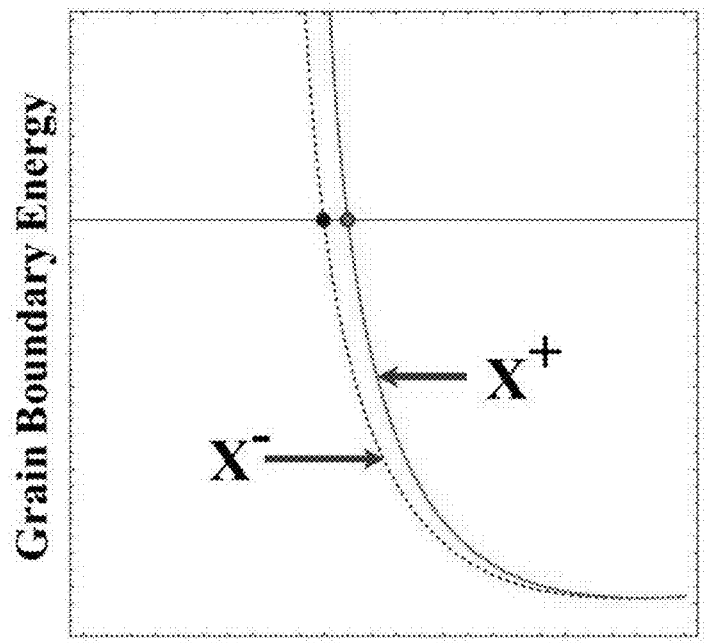

These trends may also be examined on other axes if the variations in free energy are plotted with respect to global composition, X, for a fixed pair of $X_{ig}$ and d (FIG. 6). As seen in FIG. 6, there is a sharp increase in free energy upon moving to the left, and the free energy decrease is obtained by decreasing grain size to a new free-energy curve (with different values of $X_{ig}$ and d). Blue points in FIG. 6A represent the minimum in the free energy surface at each value of global composition. For the values of $X^-$ (black dashed) and $X^+$ (magenta), the values of grain size and the grain boundary solute content that comprise the minimum for that global composition are held constant while the global composition is varied. The blue line shows that the minimum points are the tangents between set $X_{ig}$/d value curves. FIG. 6B shows grain boundary energy as a function of global composition for the $X_{ig}$ and d values for the same two minima as denoted in FIG. 6A and FIG. 5.

In this embodiment, the shapes of the free energy curves in FIGS. 6A-6B are such that they are connected by a common tangent (blue line, FIG. 6A between curves at set values of $X_{ig}$ and d. The common tangent indicates that the system prefers to exist at the combination of grain size and grain boundary solute content that is the minimum of a free energy surface for a given global composition (blue circle).

Based on the aforedescribed explanation, nanocrystalline alloys in an equilibrium grain boundary segregation state may be described in the following way according to one embodiment: the minimum of the free energy surface at each global composition may be treated as a "stoichiometric line compound," represented by a point. In other words, for each composition X, there is one preferred "compound" with a given intergranular concentration and grain size, $(X_{ig}^-, d^-)$. If the global composition is changed, there is a different preferred combination $(X_{ig}^+, d^+)$, and the system resembles a different "compound." When free energy curves are plotted against X, as is traditional in the development of binary phase diagrams, then these points may be compared to the free energy functions of other competing phases.

The following general discussion refers to analysis of the stability of alloy systems with a positive heat of mixing. In at least some embodiments the analysis may be similarly carried out for ordering alloy systems, such as those with a negative heat of mixing.

Figure 7:
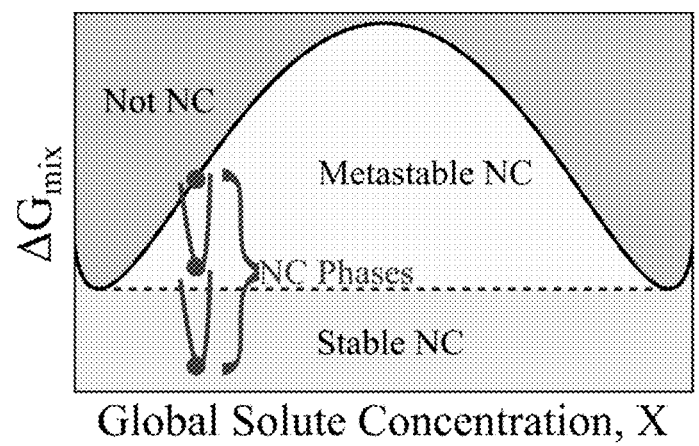
FIG. 7 shows that the free energy of the nanocrystalline (NC) phases (blue) in one embodiment can fall into three regions that are determined by the bulk regular solution (black curve) for the same materials parameters.

FIG. 7 illustrates the comparison between the minimum-energy nanocrystalline system free energy curve and those of competing phases for a positive heat of mixing alloy system. The competing phases may be, for example, classical bulk (i.e., non-nanocrystalline) phases. A schematic free energy curve for such a bulk system at a single finite temperature is shown by the solid black line in FIG. 7. This curve is for a classical phase-separating solid solution, with the two phase fields lying between the tangent points of the common tangent line (dashed black line). The results of the comparison may vary depending on the type of alloy system.

This curve, and the two phases represented by it, may be compared to the narrow U-shaped curve associated with a specific nanocrystalline state, as shown schematically by the blue curves in FIG. 7. More specifically, as described above, in some embodiments the nanocrystalline state (or phase) is viewed as a "compound" at a specific point, denoted explicitly by a blue solid point in FIG. 7. Depending upon the specific input parameters used, the location of this point may fall into one of three main regions that are delineated in FIG. 7: "stable nanocrystalline," "metastable nanocrystalline," and "nanocrystalline not supported." Those with minima at a free energy lower than the common tangent of the bulk regular solution limit are labeled as "stable nanocrystalline"; those where the minimum of the free energy surface is the trivial case of infinite grain size and the same free energy of the bulk (non-nanostructured) solid solution may occupy the "nanocrystalline not supported" region. Nanocrystalline phases that have a free energy lower than the bulk free energy curve, but higher than its common tangent are labeled as "metastable nanocrystalline." In this latter case, the nanocrystalline structure is more energetically favorable than the single phase solid solution at that solute content, but less favorable than macroscopic phase separation of the system into two solid solutions.

In some embodiments, only positive values for the grain-wise interaction parameter, $\omega_g$, that correspond to enthalpies of mixing (Eq. (6)) are employed. Note that the values of this parameter may be negative as well. The parameters may be of any value, such as between about 1 and about 2000 kJ/mol—e.g., about 1 and about 1000 kJ/mol.

In one embodiment, the combination of grain boundary energy and atomic volume divided by the grain boundary thickness to provide a parameter, $\Omega\gamma/t$, of the two pure solvent and solute species may be set to be equal; in the free energy equation, the terms containing these parameters are generally on the order of a tenth the magnitude of the other terms, and less when they appear together as a difference. In some embodiments, term $\Omega\gamma/t$ may be defined to have a value of 8.25 J/mol for both solvent and solute species, but any other value may be selected, depending on the system; for example, the values of $\Omega\gamma/t$ for some common metals are Aluminum: 6.46 J/mol, Gold: 7.7 J/mol, Copper: 8.87 J/mol, Iron: 10.6 J/mol, and Nickel: 11.5 J/mol. The value of 8.25 J/mol corresponds, for example, to a grain boundary energy of 0.5 J/m$^2$, an atomic volume of 8.25 cm$^3$/mol, and a grain boundary thickness of 0.5 nm.

The variable $\omega_{ig}$ describes the character of atomic interactions in the intergranular and transition regions (FIG. 3). In general, the grain boundary interaction parameter will be different from the grain interaction parameter. Not to be bound by any theory, but this may be the driving force for grain boundary segregation, as the enthalpy of segregation is:

$$\Delta H_{seg} = z\left[\omega_g - \omega_{ig}\left(1 - \frac{v}{1-f_{ig}}\right) - \frac{1}{z}(\Omega\gamma_B - \Omega\gamma_A)\left(1 - \frac{v}{1-f_{ig}}\right)\right] + \quad (9)$$
$$2zX_{ig}\omega_{ig}\left(1 - \frac{v}{1-f_{ig}}\right) - 2z[X_g\omega_g + v(X_{ig} - X_g)\omega_{ig}],$$

which comes from the segregation isotherm that emerges from the RNS model:

$$\frac{X_{ig}}{1-X_{ig}} = \frac{X_g}{1-X_g}\exp\left[\frac{\Delta H_{seg}}{kT}\right]. \quad (10)$$

Note that the convention is a positive value for the enthalpy of segregation for a system in which the solute preferentially segregates to the grain boundaries. If the segregation enthalpy in Eq. (9) is taken to the dilute limit:

$$\Delta H^0_{seg} = z\left(\omega_g - \frac{\omega_{ig}}{2} - \frac{(\Omega\gamma_B - \Omega\gamma_A)}{2zt}\right) \quad (11a)$$

a relationship is obtained between the parameters described herein and a dilute heat of segregation (or "enthalpy of segregation"), which is a measurable (or estimable) quantity. In some embodiments, an assumption of $\gamma_A = \gamma_B$ may be employed to reduce the equation further to:

$$\Delta H^0_{seg} = z\left(\omega_g - \frac{\omega_{ig}}{2}\right). \quad (11b)$$

The grain boundary interaction parameter may be varied to give an enthalpy of segregation, $\Delta H^0_{seg}$, between 1 and 200 kJ/mol. Depending on the system, other values may also be obtained. Given the other values for the parameters appearing in Eq. (11), this means that $\omega_{ig}$ can take on values both positive and negative. Depending on the magnitude of $\omega_g$, a strongly segregating system would have either a positive grain boundary interaction parameter of significantly less magnitude than $\omega_g$ or a negative grain boundary interaction parameter.

The systems and methods described herein allow the two interaction parameters to be varied at high resolution (down to intervals of 0.001 eV) across the ranges described above, and the minimum free energy curves for multiple compositions to be calculated across the full range of compositions (X=0 to 1). As shown below, the free energy curves for over 100 compositions were calculated. These minima are plotted against the bulk regular solution free energy curve with the same values of $\omega_g$ and z (as in FIG. 7).

The thermodynamic parameters described herein may be a function of temperature; thus the values thereof may vary with the temperatures at which they are measured. The temperature may be predetermined at any suitable values. For example, the temperature may be about 1700 K, about 1600 K, about 1500 K, about 1400 K, about 1300 K, about 1200 K, about 1100 K, about 1000 K, about 900 K, about 800 K, about 700 K, about 600 K, about 500 K, about 400 K, or about 300 K. In positive enthalpy of mixing systems the temperature may be defined as a function of a critical temperature ($T_{cr}$) defined at the top of a miscibility gap in phase-separating systems, and may be related to other parameters by the relationship ($T_{cr} = z\omega_g/2R$). For example, the temperature may be about 0.35 $T_{cr}$, 0.5 $T_{cr}$, 0.65 $T_{cr}$, and 0.85 $T_{cr}$. The temperature may be any other suitable temperatures.

In ordering alloy systems, such as those with a negative heat of mixing, there is no characteristic temperature that may be related to the other inputs in the manner that $T_{cr}$ may be for positive enthalpy of mixing alloy systems. Thus, analysis of the stability of ordering alloy systems in at least some embodiments may be performed for an absolute temperature.

Nanocrystalline Stability Map

One embodiment provides an article that may contain a diagram showing a map of stability associated with a nanocrystalline phase; in some embodiments herein the diagram is referred to as a "nanocrystalline stability map."

The diagram may take any form. FIGS. 13-18B provide examples of such diagrams in various embodiments, which are discussed further below. As shown in the figures, the diagram may delineate a plurality of regions respectively representing different stable phases of at least one binary alloy. The different phases may be any of the phases described above.

In some embodiments, the respective regions of the plurality of regions are delineated by at least one boundary determined as a function of at least two thermodynamic parameters associated with grain growth and phase separation of the at least one binary alloy. In an ordering alloy system, the respective regions of the plurality of regions may be delineated by at least one boundary determined as a function of at least three thermodynamic parameters associated with grain boundary segregation, phase separation, and intermetallic compound formation of the ordering alloy system.

While the construction of the map is described in a later section, the different regions of the map in one embodiment are described below.

Non-Nanocrystalline (No Stability)

In some embodiments, there may be two cases in which a system has no stable nanocrystalline configuration. The first case may occur when there is no free energy curve with a minimum at a finite grain size for any of the possible compositions. FIG. 4B depicts this situation. This situation may arise in cases where the heat of segregation is insufficiently large with respect to the value of the heat of mixing, and as a result, no energy minimum exists over the entire range of composition because the alloying interactions in the grain boundary are not sufficiently different from those in the grains to drive solute segregation.

The second case may occur for systems that have nanocrystalline energy minima across a wide range of compositions (and energies either stable or metastable with respect to phase separation) but still have composition ranges where the nanocrystalline state is not stable. For example, when the global composition is below the solubility limit, no stable nanocrystalline compounds are identified. In other words, in phase-separating alloys, supersaturated solid solutions are needed to achieve a nanocrystalline structure stable against grain growth. Note that some of the prior analytical models of segregation in nanocrystalline systems, such as those by Weismuller and Kirchheim, are developed with the assumption of a dilute limit. The model described herein shows that such an assumption may be problematic for at least some alloy systems with non-dilute solubility limits, as in at least some of the alloy systems provided herein. The models described herein do not suffer such a deficiency.

Stable Nanocrystalline

Figure 14:
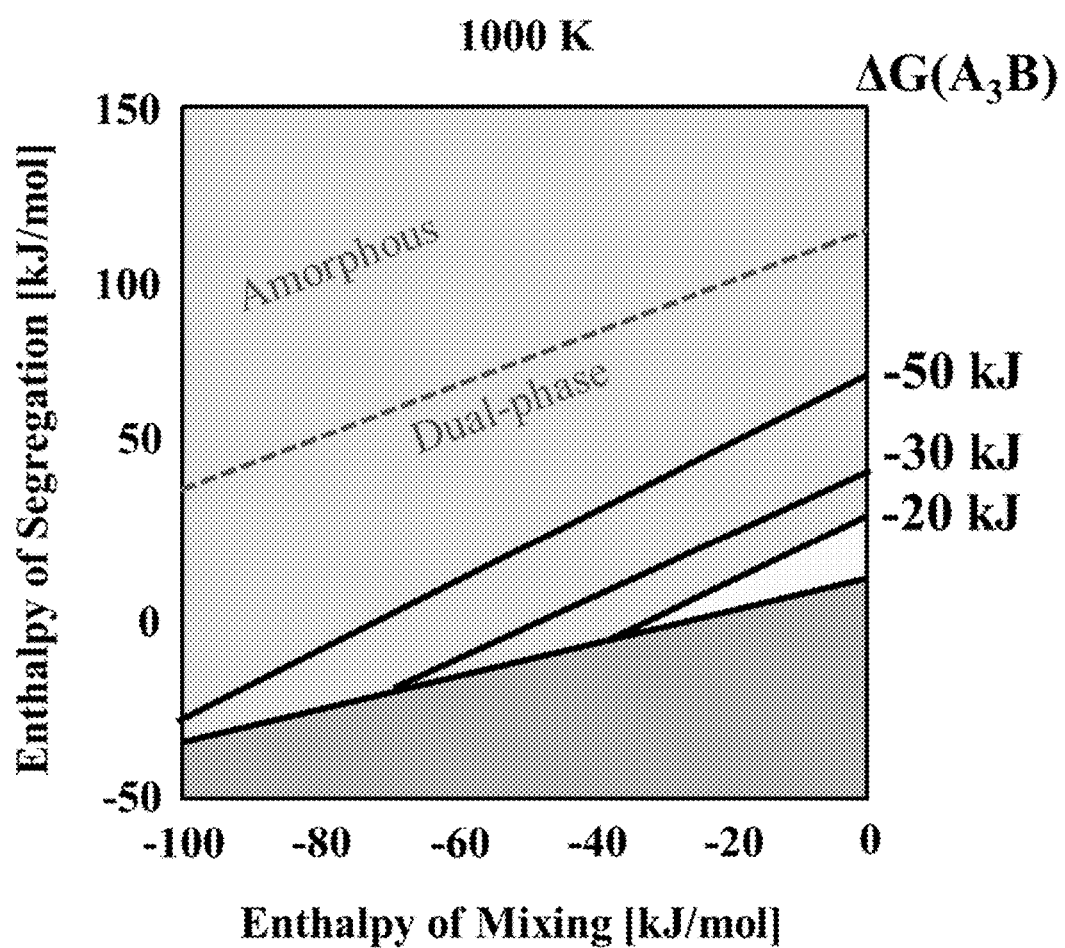
FIG. 14 shows a nanocrystalline stability map according to one embodiment for an ordering alloy system containing an $A_3B$ compound with a free energy of −20 kJ/mol, −30 kJ/mol and −50 kJ/mol at a temperature of 1000 K. Green region: stable NC microstructure; yellow region: metastable NC microstructure; red region: no stable NC microstructure.
Figure 15:
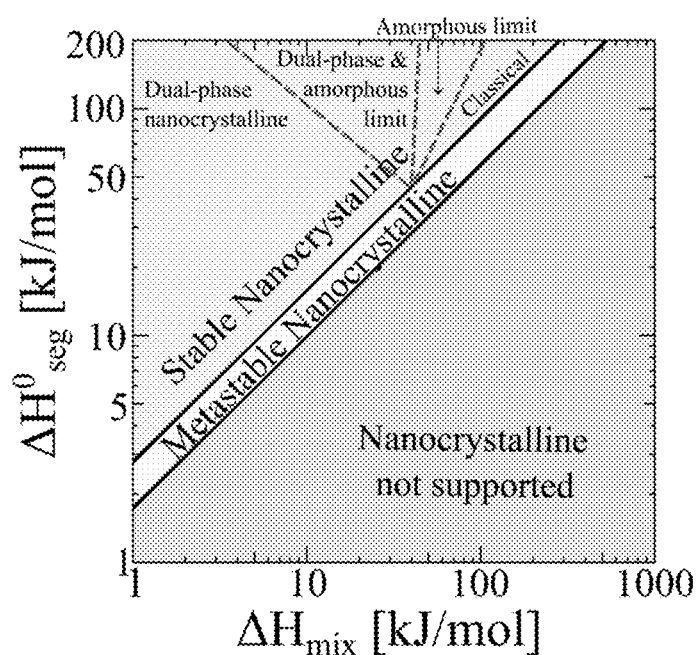
FIG. 15 shows a nanocrystalline stability map according to one embodiment, showing delineated regions of stability (green), metastability (yellow), and no stability (red) in binary alloys as a function of their enthalpies of mixing and segregation.
Figure 16:
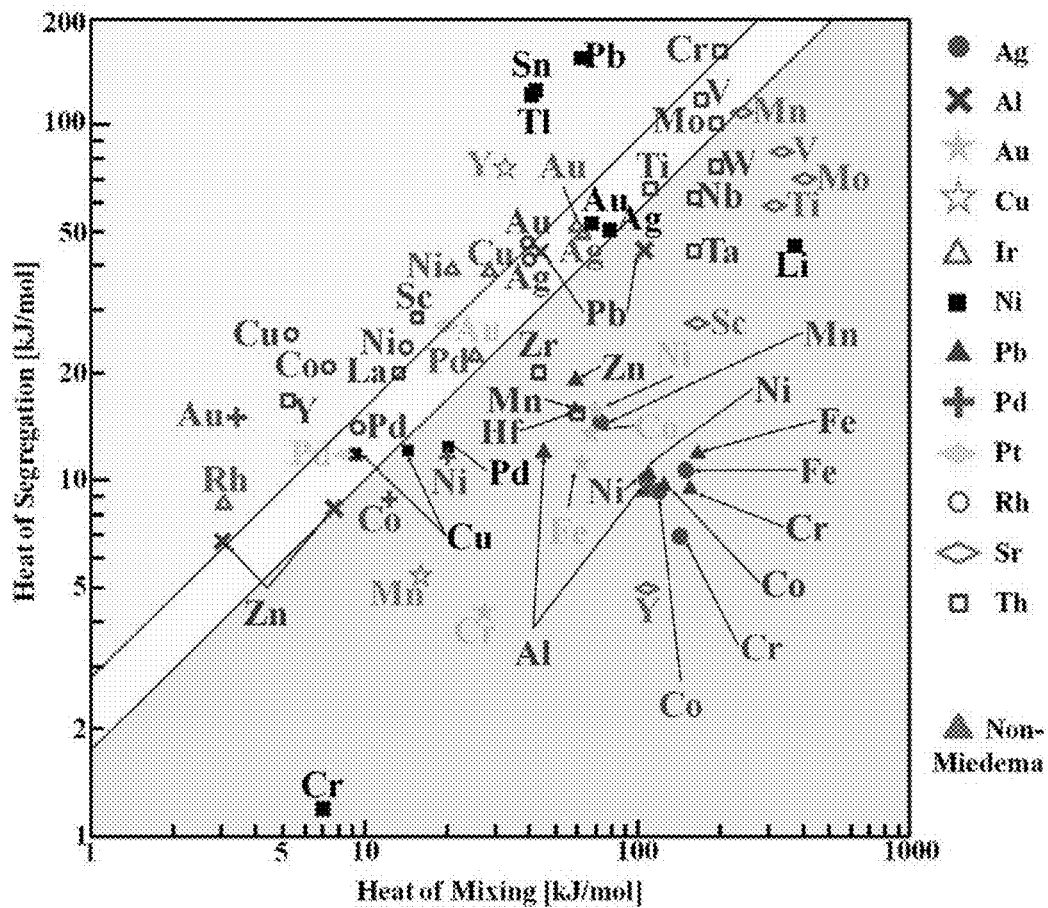
FIG. 16 shows a nanocrystalline stability map according to one embodiment for face-centered cubic (FCC) binary alloys at a temperature of 0.35 $T_{cr}$. Green region: stable NC microstructure; yellow region: metastable NC microstructure; red region: no stable NC microstructure.
Figure 17A:
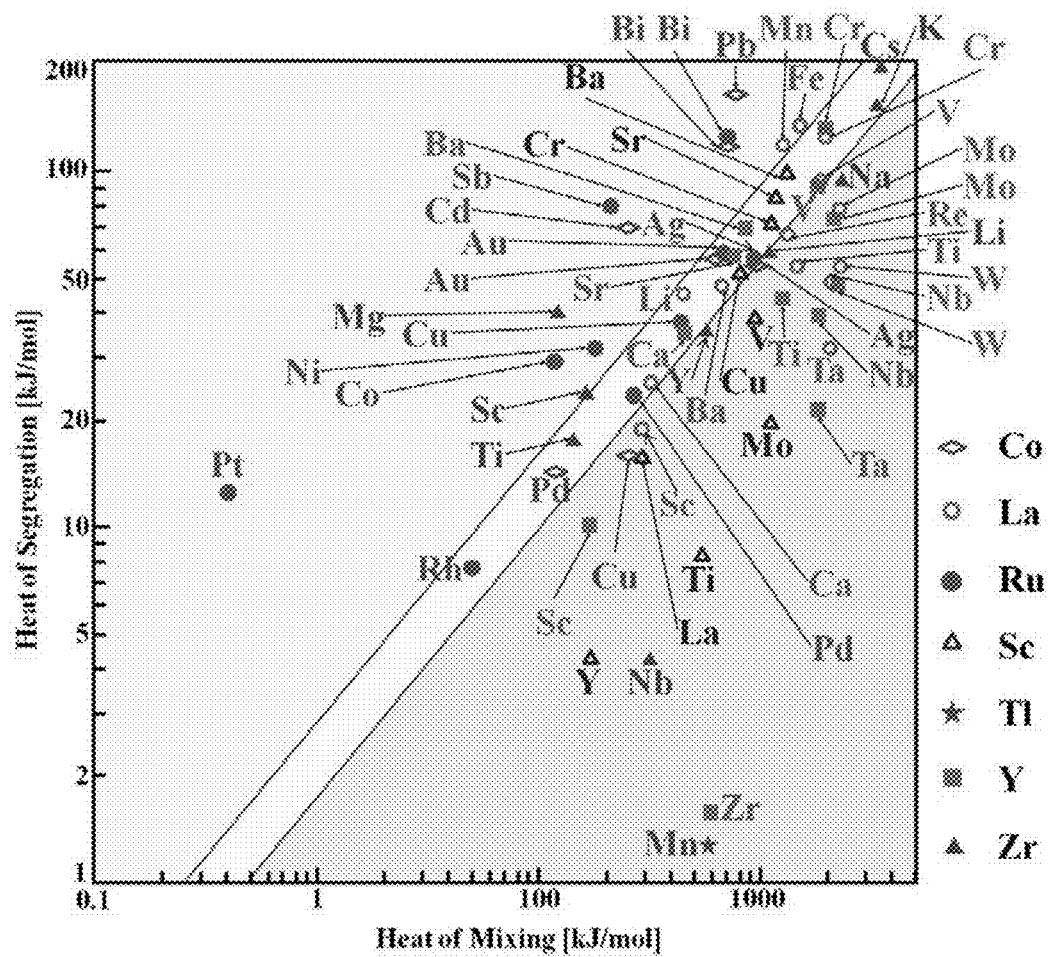
FIGS. 17A-17B show two exemplary nanocrystalline stability maps according to one embodiment for different hexagonal closed-pack (HCP) binary alloys at a temperature of 0.35 $T_{cr}$. Green region: stable NC microstructure; yellow region: metastable NC microstructure; red region: no stable NC microstructure.
Figure 17B:
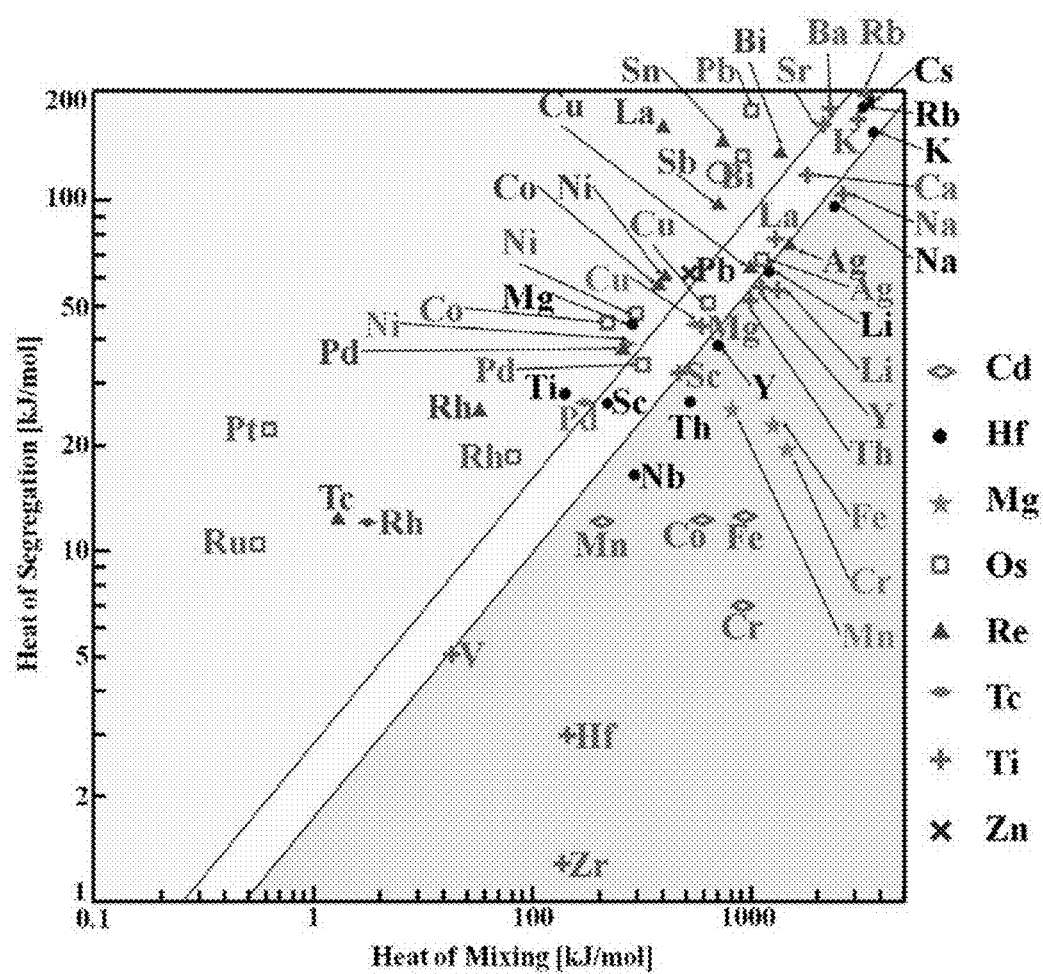
Figures 18A, 18B:
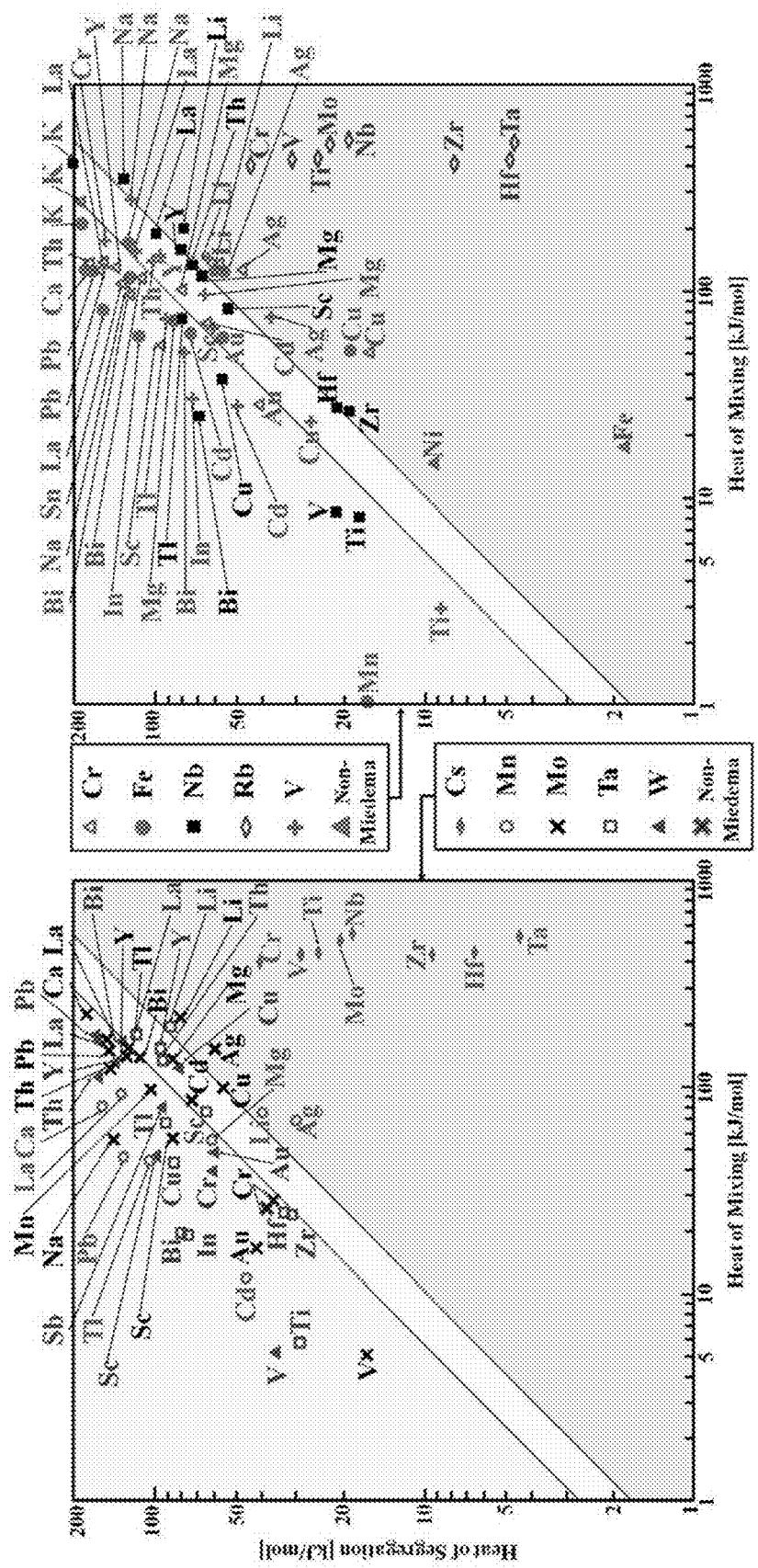
FIGS. 18A-18B show a nanocrystalline stability map according to one embodiment for body-centered cubic (BCC) binary alloys at a temperature of 0.35 $T_{cr}$. Green region: stable NC microstructure; yellow region: metastable NC microstructure; red region: no stable NC microstructure.

The types of nanostructures that are thermodynamically stable may be diverse. Accordingly, as shown in FIGS. 15 and 14, the stable nanocrystalline phase may be further divided into sub-regions. In at least some embodiments, the stable phase of an ordering alloy system, such as one with a negative heat of mixing, may include at least one of: dual-phase nanocrystalline; dual-phase nanocrystalline and amorphous phase; and an amorphous phase as depicted in a nanocrystalline stability map. In one embodiment, the stable phase of an ordering alloy system may consist of these phases. The stable phase of an alloy system with a positive heat of mixing may include at least one of dual-phase nanocrystalline; dual-phase nanocrystalline and amorphous phase; an amorphous phase; and a classical segregation-stabilized nanocrystalline phase, as may be depicted in a nanocrystalline stability map.

Classical Segregation-Stabilized Nanocrystalline Region

A classical segregation-stabilized nanocrystalline region may not be produced for ordering alloy systems with a negative heat of mixing. By contrast, a classical segregation-stabilized nanocrystalline region may be found in at least some embodiments of alloy systems with a positive heat of mixing, as described below.

In some embodiments of alloy systems with positive heats of mixing, for some combinations of high heats of mixing and high heats of segregation, the condition of segregation-based nanostructure stabilization envisioned by Weissmuller may be achieved. In these cases the relationship between the enthalpies is such that the grain boundary interaction parameter approaches ideal behavior, namely $\omega_{ig}=0$.

Figure 8A:
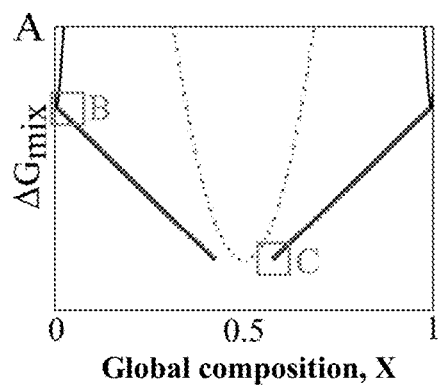
FIGS. 8A-8D show in one embodiment: (a) free energy comparison of regular solution (black curve), amorphous phase limit (green dashed curve), and the nanocrystalline points (blue circles) for the "classical nanocrystalline" case; (b) an enlarged view of the free energy comparison of nanocrystalline points as they approach the regular solution at the solubility limit, in the region marked in (a); (c) an enlarged scale free energy comparison of the terminus of the nanocrystalline points as indicated by the box in (a)—the final composition that supports a nanocrystalline phase due to the ($X_{ig}$, d) space limitation is seen with respect to global composition; (d) grain size versus global composition.

A representative free energy curve comparison in one embodiment of an alloy system with a positive heat of mixing is provided in FIG. 8A. Each blue point in the figure represents a nanocrystalline "compound." FIG. 8A shows free energy comparison of regular solution (black curve), amorphous phase (green dashed curve), and the nanocrystalline points (blue circles) for the "classical nanocrystalline" case; this example case has a non-limiting exemplary enthalpy of mixing of 81 kJ/mol and enthalpy of segregation of 79 kJ/mol.

Figure 8B:
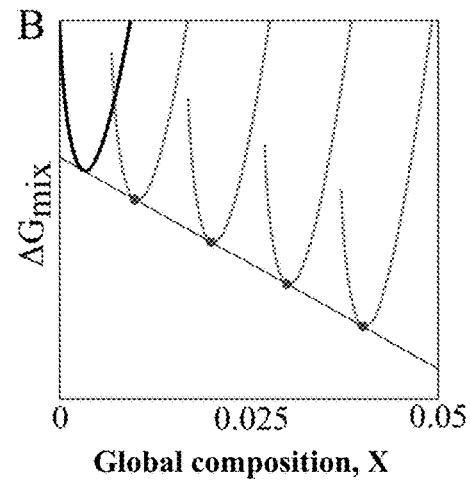
Figure 8C:
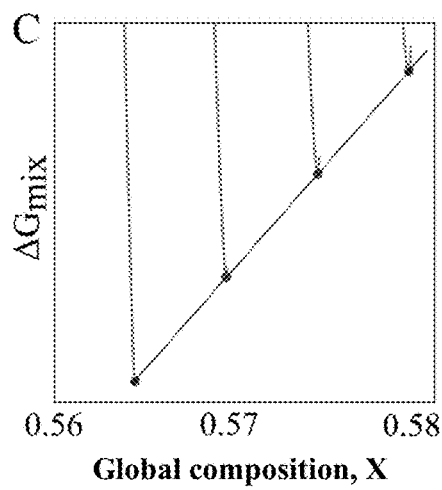
Figure 8D:
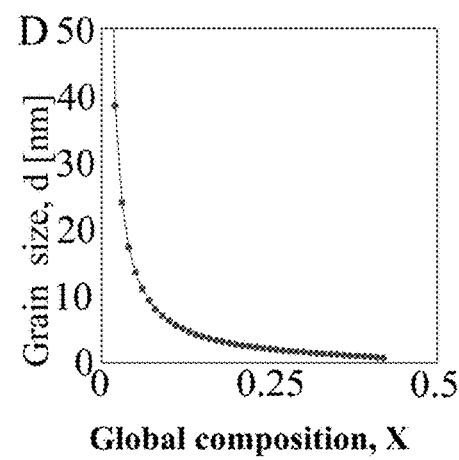

In the magnified views of FIGS. 8B and 8C, the local free-energy curves corresponding to a few such points are illustrated; the points corresponding to the stable condition all lie on a single common tangent line. The points shown are only examples, and there are in fact an infinite number of them between any two of those shown; the locus of the points represents a smooth continuum of stable grain sizes that are a monotonic function of the composition. In one embodiment, the grain size decreases with increasing solute content in the relationship often observed in experimental systems, as depicted in FIG. 8D.

In some embodiments, there is a well-defined composition range with clear upper and lower bounds or limits with respect to solute concentration, over which a nanocrystalline phase is stable. The limits and thus the boundaries set by the limits across a range of parameters as shown on a stability map may be determined by a plurality of thermodynamic parameters, such as those described above. For example, at low solute concentrations, the existence of nanocrystalline phase is bounded by the solubility limit, below which no nanocrystalline minima exist. This is already discussed above and may be seen graphically in the magnified view of FIG. 8B. For high solute concentrations, the limiting composition may be seen based on Eq. (2). For a given global composition, there is a limit to the $(X_{ig}, d)$ combinations that may be supported while conforming to Eq. (2); if all of the solute is present in the grain boundaries and none in the grain interiors, $X=f_{ig}X_{ig}$ restricts the smallest grain size and largest value of solute allowable for a stable nanocrystalline phase. This limitation may create boundaries on the free energy surface, beyond which no surface exists. See e.g., FIG. 4A (on the left-hand side where the smallest grain sizes cannot be accessed on the free energy surface). This truncation of the free energy curves can also be seen in the magnified view in FIG. 8C, which shows the points for the nanocrystalline states close to the limiting composition, as well as their individual free energy curves; note that these are all truncated on the left-hand side, at the limits achievable by Eq. (2). The truncation becomes more pronounced as the concentration rises, and the last nanocrystalline compound—that with the largest possible solute content—is the last that has a minimum in the free energy surface contained within the available range of grain size and solute distribution (FIG. 8C). In one embodiment, this compound may be referred to as the "terminal" nanocrystalline structure.

The series of blue points that all lie on a common "nanocrystal free energy line" are a common feature of many systems, and the arrangement of these lines in the free energy diagram may lead to several possible situations. In the case pictured in FIG. 8A, for example, these lines end at the terminal nanocrystalline structure, leaving a gap between their ends. These terminal structures have the lowest free energy in the system, far lower than that of the bulk regular solution. The nanocrystalline phases in this system are also in equilibrium with the bulk regular solution phase. For non-dilute alloys, there is a miscibility gap that separates the terminal solvent-rich nanocrystalline compound and its counterpart terminal solute-rich nanocrystalline compound. In some embodiments, these nanocrystalline compounds are symmetric, due to the assumption of equal $\Omega\gamma/t$ for solvent and solute. As noted above, different assumptions, and thus different shapes of the graphs for the nanocrystalline compounds, may exist.

For the exemplary system presented in this figure, another apparent "phase" is observed, shown by the green dashed line in FIG. 8A. This free energy curve corresponds to the intergranular regular solution (Eq. (8))—the limit of the RNS model as grain size, d, approaches the grain boundary width, t (i.e., as the system approaches the "amorphous limit" where the material is entirely composed of intergranular state). The situation may arise where the amorphous limit can be lower in energy in the central composition region where nanocrystalline states are not supported due to the $(X_{ig},d)$-space limitations.

For these cases in the classical region, this may lead to equilibrium between the terminal nanocrystalline compound and the amorphous limit phase (similarly, between the amorphous limit phase and the right hand terminal nanocrystalline compound). The case where the amorphous limit exhibits a lower free energy than the nanocrystalline points such that it forms the lowest common tangent with the bulk regular solution is discussed in the following section.

Amorphous Phase

Figure 9:
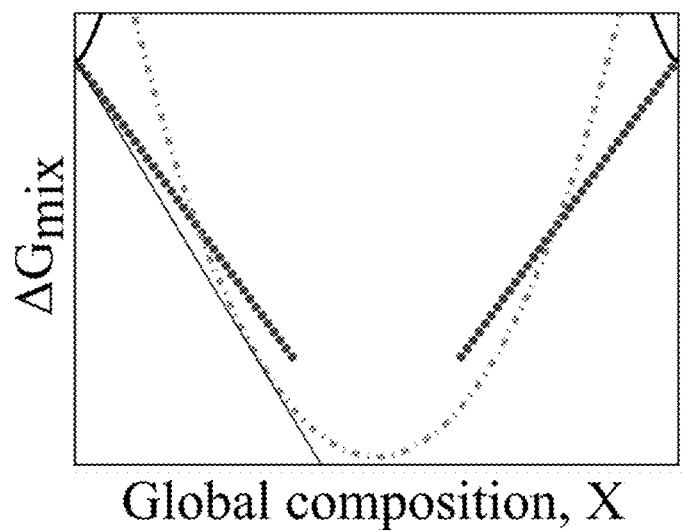
FIG. 9 illustrates that the free energy of the amorphous phase (green dashed curve) is lower than that of the bulk regular solution (black curve) and the nanocrystalline points (blue circles) in one embodiment.

In some embodiments, the "intergranular phase" described above has the lowest free energy curve. As shown in FIG. 9, this curve may fall below the free energy lines of the nanocrystalline structures. This example has a non-limiting exemplary enthalpy of mixing of 93 kJ/mol and enthalpy of segregation of 104 kJ/mol, but similar behavior may be observed in ordering alloy systems with a negative enthalpy of mixing. This situation may arise when the grain boundary interaction parameter is negative and the grain interaction parameter is positive; this drives the preference for intergranular regions over crystalline ones. That the intergranular term of the RNS could in fact have the lowest free energy of any other possible state suggests that there are positive and negative heat of mixing systems in which an "amorphous" state is stable (due to its relatively lower heat of mixing). As shown in FIG. 9, when the intergranular phase is the lowest free energy state, it is in equilibrium with the bulk regular solution. Not to be bound by any particular theory, but this may be related to a common metric for assessing binary amorphous systems: the Glass Forming Range ("GFR"). There are a number of approaches to estimate the GFR (i.e. size/structure difference, eutectic shape, and enthalpy models) and the model described herein provides an alternative.

Dual-Phase Nanocrystalline

Figure 10A:
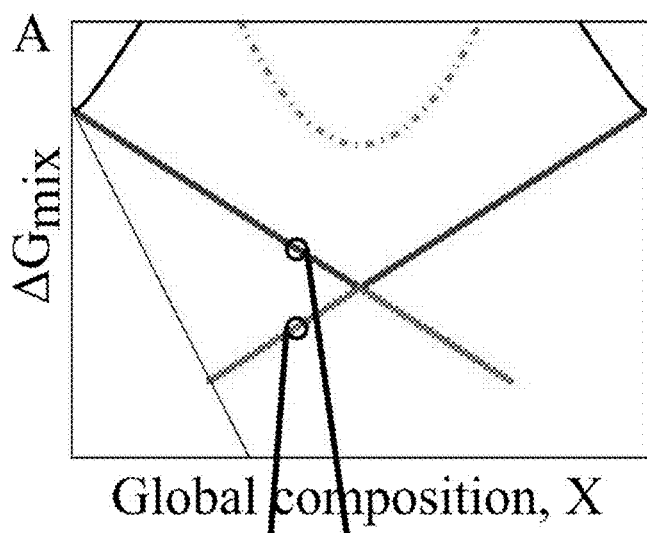
FIGS. 10A-10C show in one embodiment: (a) free energy plot showing regular solution (black curve), nanocrystalline phases with solute rich grain boundaries (blue circles), and nanocrystalline phases where the solvent has become the grain boundary element (red diamonds); (b) free energy surface for a given global solute composition showing the two minima; (c) schematic of the nanostructure rearrangement from solvent rich grains to solute rich grains.
Figure 10B:
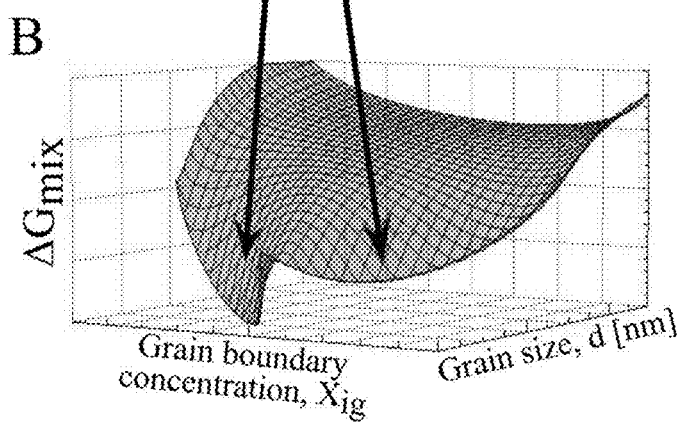
Figure 10C:
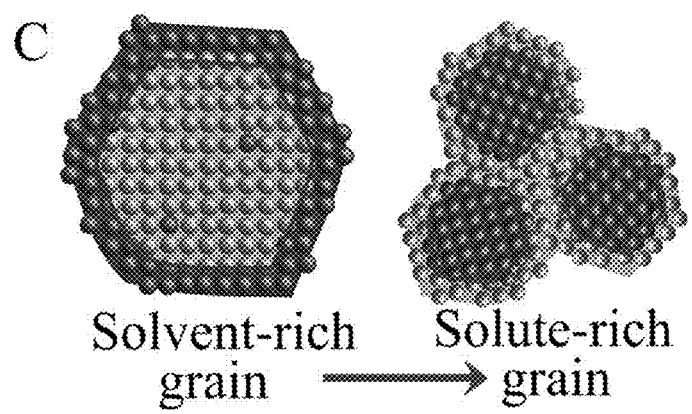

In some embodiments, when the heat of segregation is larger than the heat of mixing, such that $\omega_{ig}$ is negative, but not sufficient to drive the system to the amorphous limit, the free energy surface at a given composition (FIG. 10B) may support two minima where the grain boundary energy is zero; hence the designation "dual-phase nanocrystalline." FIG. 10A shows a free energy plot of an alloy system with a positive heat of mixing showing regular solution (black curve), nanocrystalline phases with solute rich grain boundaries (blue circles), and nanocrystalline phases where the solvent has become the grain boundary element (red diamonds); this example has a non-limiting exemplary enthalpy of mixing of 23 kJ/mol and enthalpy of segregation of 35 kJ/mol, but similar dual-phase nanocrystalline regions may be present in ordering alloy systems with negative heats of mixing. In this alloy system, one of these minima is the classic grain boundary segregation-stabilized state (i.e., the solute is strongly segregated to the grain boundaries, and the stabilized grain size continues to decrease with an increase in composition along the nanocrystal free energy line). The second minimum has solute-rich grains with the solvent segregated to the grain boundary. Because $\omega_{ig}$ also describes the cross-interactions between the crystalline and intergranular regions (see FIG. 3), a mildly negative value of this parameter may lead the system to maximize unlike bonds crossing between these regions. This in turn may promote a finer grain size, and in order to support the increased grain boundary volume, the intergranular region must be occupied by the solvent element. Thus, the roles of solute and solvent are exchanged and the preferred system becomes a "solute nanocrystalline phase." The composition range of such solute nanocrystalline phases is limited by the same ($X_{ig}$, d)-space constraints as the classical "solvent" nanocrystalline phases. In some embodiments, the solute nanocrystalline phases may also follow a composition-grain size relationship; however, as the solute concentration decreases from the equiatomic concentration, the grain size decreases.

While this case is described as "dual-phase nanocrystalline" due to the existence of two nanocrystalline phases stable against grain growth at a single composition, the solute nanocrystalline phase may be lower in free energy. Constructing common tangents on FIGS. 10A-10C may lead to a conclusion that over a broad range of compositions the solute nanocrystalline phase is in equilibrium with the bulk regular solution; on the solvent rich side of the phase diagram, the stable states are a solvent rich solid solution and a solute rich nanocrystalline phase with grain boundary segregation. In the middle of the diagram, the equilibrium is between two solute nanocrystalline phases, which may be an interesting dual-phase nanocomposite that would in general be a true stable bimodal structure.

Dual-Phase Nanocrystalline/Amorphous Structures

Figure 11:
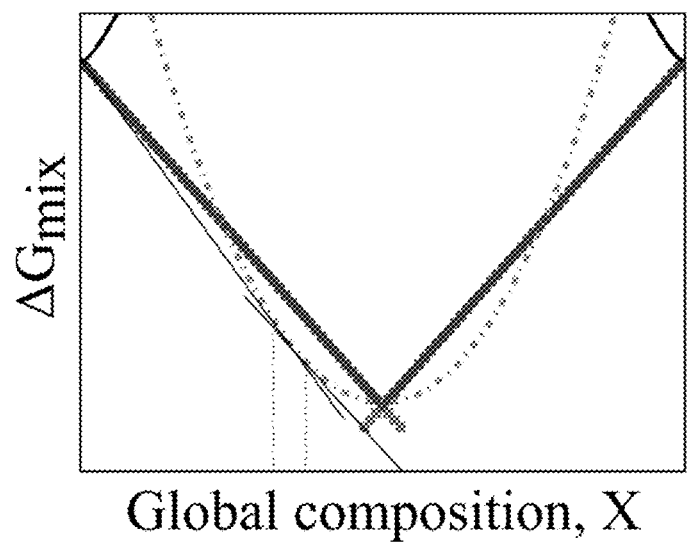
FIG. 11 shows a free energy plot for one embodiment where the amorphous limit (green dashed curve) appears below the common tangent (thin black line) between the regular solution (thick black curve) and nanocrystalline phases (solvent nanocrystalline phases in blue; solute nanocrystalline phases in red diamonds).

The cases where the nanocrystalline points compete with an amorphous phase, or with one another (solute nanocrystalline phase), have been provided above. These cases correspond to a relatively higher and relatively lower heat of mixing, respectively. Between these two cases may be a condition in which both the intergranular free energy curve (amorphous limit) and the terminal compositions of the nanocrystalline free energy lines are stable. An example of this situation is shown in FIG. 11, where the low energy of the intergranular regions places it in equilibrium with the bulk regular solution at low solute levels. This example has a non-limiting, exemplary positive enthalpy of mixing of 58 kJ/mol and enthalpy of segregation of 75 kJ/mol. Similar dual-phase nanocrystalline and amorphous structures may be present in ordering alloy systems with a negative enthalpy of mixing. At higher concentrations, the amorphous limit may be in equilibrium with the solute nanocrystalline phase defined by the terminal structures of the nanocrystal free energy lines. The two solute nanocrystalline phases may be in equilibrium around the equiatomic composition.

Metastable Nanocrystalline

Figure 12A:
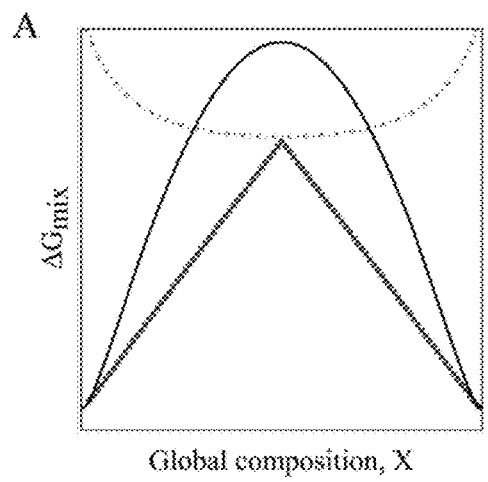
FIGS. 12A-12D show in one embodiment: (a) a free energy comparison of regular solution (black curve) and nanocrystalline points (blue circles); (b) grain size as a function of the global solute concentration in a metastable nanocrystalline binary alloy; (c) similar to FIGS. 6A-6B, the minima for two compositions are plotted as points, while the curves represent the free energy as a function of composition if the $X_{ig}$ and d values for those minima are held constant; (d) grain boundary energy as a function of global composition for the $X_{ig}$ and d values for the same two minima as denoted in (a).

In some embodiments, the stable phase is a metastable nanocrystalline structure. In the case of metastable nanocrystalline structures of alloy systems, the RNS model may exhibit a minimum energy in the d-X space, and grain size may decrease with composition in a relationship similar to other model predictions and experimental data. However, these states may be unstable with respect to macroscopic phase separation into the bulk phases. FIG. 12A depicts the free energy diagram of such a system in an alloy system with a positive heat of mixing, which system contains nanocrystalline free energy lines that lie below the regular solution free energy curve, but above the common tangent denoting bulk phase separation (the yellow region of FIG. 7). This example has a non-limiting enthalpy of mixing of 58 kJ/mol and enthalpy of segregation of 49 kJ/mol. A nanocrystalline system in this condition would be stable against grain growth but would lower its energy via phase separation on the bulk scale.

Figure 12B:
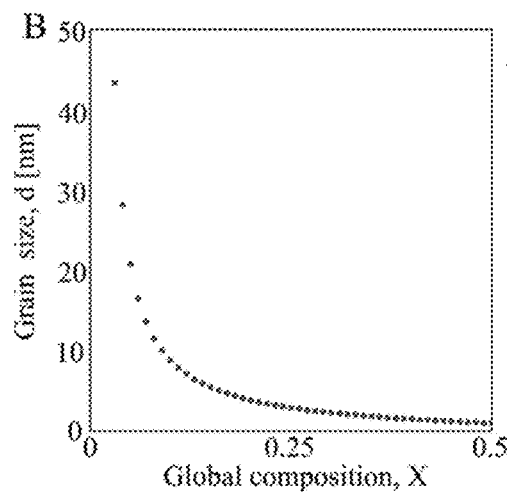
Figure 12C:
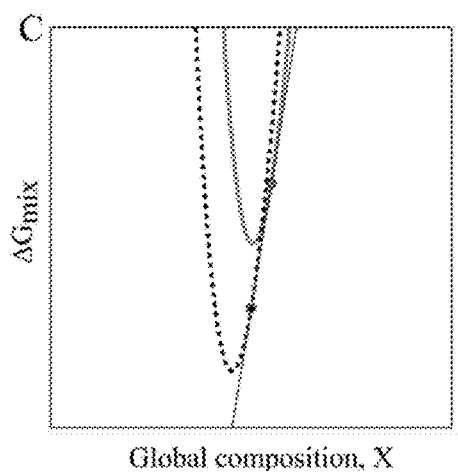
Figure 12D:
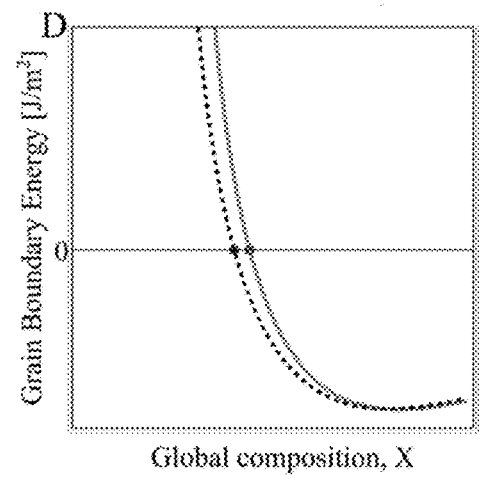

For the metastable case in alloy systems with a positive enthalpy of mixing, for an increase in composition, the free energy increases rapidly; for a decrease in composition, the grain boundary energy is positive, and as a result the system favors grain growth (FIGS. 12C-12D). This pattern continues until the infinite grain size of the regular solution is obtained (FIG. 12B). At the nanocrystalline compound values of $X_{ig}$ and d the grain boundary energy is reduced to zero, reducing the drive for grain growth, but the free energy of a system with a larger grain size may be a lower free energy state. At the same time, the lower free-energy of the common-tangent bulk phases may favor phase separation in the structure, such that the equilibrium structure becomes a coarse-grained, phase separated system.

In ordering alloy systems with a negative mixing enthalpy, the free energy of the ordered compound may confer metastability to the ordered alloy system. In some cases, nanocrystalline structures that are stable with respect to a bulk solid solution phase may be metastable with respect to compound phase formation and precipitation.

In some embodiments of an ordering alloy system with a negative heat of mixing, the stable phase may be a locally metastable nanocrystalline structure. A locally metastable phase may exist when a minimum in the free energy surface where the grain boundary energy is zero is present as a local minimum as opposed to a global minimum, signifying that the lowest possible free energy for the composition is the bulk regular solution with infinite grain size. FIG. 2A depicts a local minimum in a free energy surface, and FIG. 2B depicts the local minimum relative to other phases in the composition. In at least some embodiments, locally metastable phases may exist in ordering alloy systems with negative mixing enthalpy.

Applications

The aforedescribed methods and models may be employed to identify the stable phase of an ordering alloy system; in some embodiments the ordering alloy system is an ordering binary alloy system. For example, the methods and models described herein may be able to identify whether an ordering binary alloy system would be stable as a nanocrystalline alloy (or in a nanocrystalline phase). Further, by using certain thermodynamic parameters, the methods and models described in some embodiments herein allow identification of any ordering binary alloy system that may be stable (against both grain growth and phase separation) as a nanocrystalline ordering alloy system. The methods and models described herein are versatile and may be applicable to any type of ordering alloy systems. Also, any of the steps in the model described herein may be repeated for a plurality of ordering binary alloy systems.

By using the methods, systems, and articles provided herein, ordering binary alloy systems that may be stable as a stable nanocrystalline ordering alloy system may be identified. Once an alloy that is identified as one that may be stable as a nanocrystalline ordering alloy system, the ordering alloy system may be fabricated. Any fabrication technique suitable for the particular ordering alloy system may be employed. For example, the technique may be electrodeposition, physical or chemical vapor deposition, plasma spraying, mechanical alloying and other powder-based production routes, casting, solidification, or any other suitable fabrication technique.

As described in the section below, a nanocrystalline stability map may be constructed by determining the boundaries of the stability regions and then comparing the thermodynamic parameters of an ordering binary alloy system against the boundaries to determine the stable phase of the ordering binary alloy system—stable nanocrystalline, metastable nanocrystalline, or non-nanocrystalline. In other words, by comparing the thermodynamic parameters of an ordering binary alloy system against predetermined values (i.e., the boundaries), the stable phase of the ordering binary alloy system may be identified.

The generation and population of data points into the nanocrystalline stability map may be automated. For example, the method can be automated by a software program executable by an information processor, such as a computer. The information processor may be a part of a system that includes (i) at least one memory storing processor-executable instructions and (ii) at least one information processor coupled to the at least one memory, wherein upon execution of the processor-executable instructions the processor implements the methods described herein. In some embodiments, the system includes a computer, which includes a processor connected to a bus. Input/output (I/O) devices are also connected to the bus, and can include a keyboard, mouse, display, and the like. An executable program including a set of processor-executable instructions for identifying stable binary alloy phases as described above is stored in memory, which is also connected to the bus. In one embodiment, a program that can execute the presently claimed methods is recorded on a non-transitory computer-readable recording medium, such as a compact disc (CD), floppy diskette, or DVD.

NON-LIMITING WORKING EXAMPLE

Example 1

Nanocrystalline Stability Map for Ordered Alloy Systems

Figure 13:
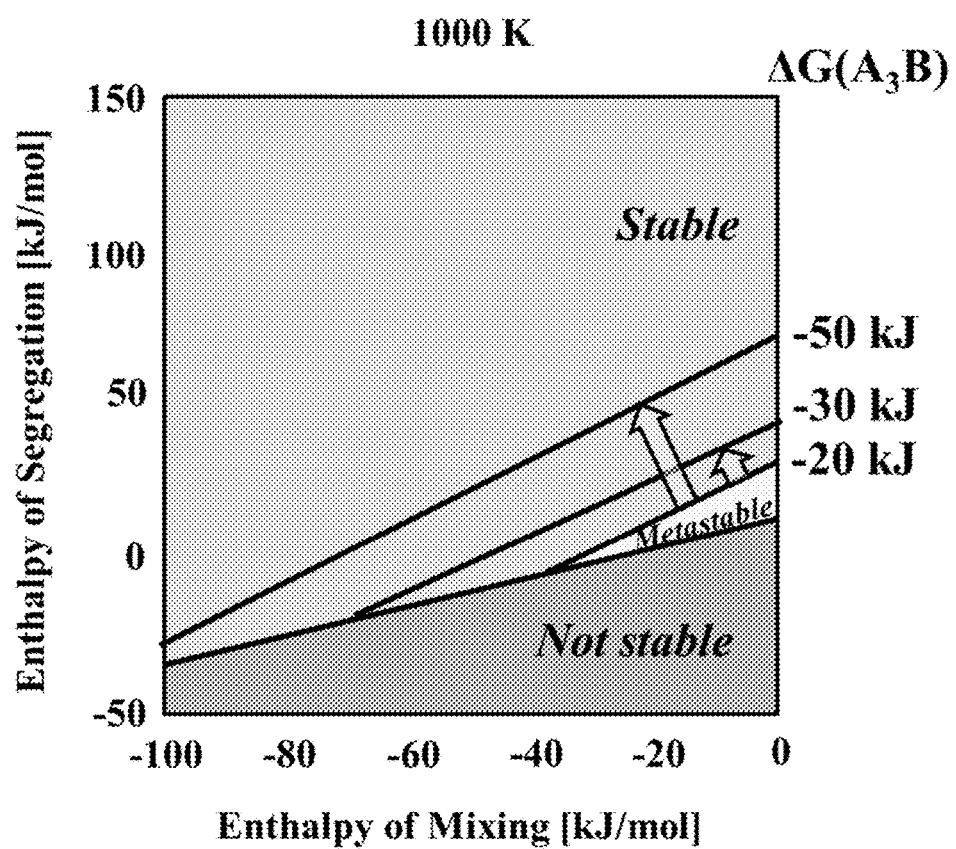
FIG. 13 shows a nanocrystalline stability map according to one embodiment for an ordering alloy system containing an $A_3B$ compound with a free energy of −20 kJ/mol, −30 kJ/mol and −50 kJ/mol at a temperature of 1000 K. Green region: stable NC microstructure; yellow region: metastable NC microstructure; red region: no stable NC microstructure.

A nanocrystalline stability map was constructed by determining at least three thermodynamic parameters, and comparing the at least three thermodynamic parameters with a predetermined set of respective thermodynamic parameters to identify stable phases. A number of these comparisons were combined to form a stability map, as depicted in FIG. 13. The at least three thermodynamic parameters may be associated with grain boundary segregation, phase separation, and intermetallic compound formation of the ordering alloy system. The nanocrystalline stability map includes a stable nanocrystalline phase region, a metastable nanocrystalline phase region, and a non-nanocrystalline phase region.

The boundary of the non-nanocrystalline phase region of the nanocrystalline stability map is determined by a relationship:

$$\Delta H_{seg} = a\Delta H_{mix} + c,$$

wherein $\Delta H_{mix}$ and $\Delta H_{seg}$ each independently represents an enthalpy of mixing and an enthalpy of segregation as respectively two of the at least three thermodynamic parameters, a and c each independently represents a slope and an intercept of the boundary, respectively.

The boundary of the stable nanocrystalline phase region of the nanocrystalline stability map is determined by a relationship:

$$\Delta H_{seg} = a_i\Delta H_{mix} + c_i,$$

wherein $\Delta H_{mix}$ and $\Delta H_{seg}$ each independently represents an enthalpy of mixing and an enthalpy of segregation as respectively two of the at least three thermodynamic parameters, $a_i$ and $c_i$ each independently represents a slope and an intercept of the boundary for the ith value of a third thermodynamic parameter. The third thermodynamic parameter may be a free energy of formation of an intermetallic compound of the ordering alloy system, and each value of the third thermodynamic parameter then corresponds to a different free energy of formation value. FIG. 13 depicts a nanocrystalline stability map with boundaries of the stable nanocrystalline phase region for three different energy of formation values.

The metastable nanocrystalline region of the nanocrystalline stability map is the region between the stable nanocrystalline boundary and the non-nanocrystalline region boundary. As depicted in FIG. 13, the size of the metastable nanocrystalline region increases as the free energy of formation of an intermetallic compound decreases.

The stable nanocrystalline phase region may include sub-regions denoting a dual-phase nanocrystalline phase, a dual-phase nanocrystalline phase and amorphous phase, and an amorphous phase. The stable region may include both a dual-phase nanocrystalline sub-region and an amorphous phase sub-region, with the dual-phase nanocrystalline region being adjacent to the boundary of the stable nanocrystalline phase region. FIG. 14 depicts a nanocrystalline stability map with a stable nanocrystalline region that includes a dual-phase nanocrystalline sub-region and an amorphous phase sub-region, with the dual-phase nanocrystalline sub-region located between the amorphous phase sub-region and the boundary of the stable nanocrystalline region.

The nanocrystalline stability map for ordered alloy systems is substantially, or entirely, free of a classical segregation-stabilized nanocrystalline phase.

Based on the stability map, at a predetermined temperature of 1000 K the following ordering binary alloy systems were found to have a stable nanocrystalline phase against grain growth and phase separation: the ordering binary alloy systems may be at least one of Ag—La, Ag—Sc, Ag—Y, Ba—Pd, Ba—Pt, Be—Ti, Bi—Pd, Ca—Pt, Cd—Pd, Co—Al, Co—As, Co—Ga, Co—Ge, Co—Hf, Co—Nb, Co—Sc, Co—Ta, Co—Ti, Co—Y, Co—Zr, Cr—Pt, Cu—Sc, Fe—Al, Fe—As, Fe—Hf, Fe—Zr, Hf—Bi, Hf—Co, Hf—Ni, Hf—Os, Hf—Re, Hf—Tl, Ir—Ge, La—Ag, La—Ir, La—Rh, La—Zn, Mn—Ga, Mn—Pd, Mn—Sb, Nb—Co, Nb—Ni, Nb—Re, Nb—Sb, Ni—Ga, Ni—Ge, Ni—Hf, Ni—La, Ni—Nb, Ni—Ta, Ni—Th, Ni—Y, Os—As, Os—V, Os—Y, Pt—Bi, Pt—Mn, Re—As, Re—Hf, Re—Nb, Re—Ta, Re—Ti, Rh—Sb, Rh—Sn, Rh—Zn, Ru—Ga, Ru—La, Ru—V, Ru—Y, Sc—Ag, Sc—Ni, Sc—Os, Sc—Ru, Sc—Tc, Sn—Pd, Sr—Pd, Sr—Pt, Ta—Ga, Ta—Ni, Ta—Re, Ta—Sb, Tc—La, Tc—Th, Tc—Y, Th—Ir, Th—Rh, Ti—Be, Ti—Bi, Ti—Co, Ti—Ni, Ti—Pb, Ti—Sn, Ti—Zn, V—Ru, V—Sb, V—Tc, W—As, W—Si, Y—Ag, Y—Ir, Y—Rh, Y—Zn, Zn—Hf, Zn—La, Zn—Sc, Zn—Y, Zr—Be, Zr—Co, Zr—Ni, and Zr—Re. Other additional ordering binary alloy systems that have not been shown in the exemplary non-limiting maps provided herein may exist.

The following ordering binary alloy systems were found to have a metastable nanocrystalline phase at 1000 K: the ordering binary alloy systems may be at least one of Fe—Sc, Hf—Ag, Ir—Cd, Ir—Cr, Ir—In, Ir—Mg, Ir—Mn, Ir—Sb, Ir—Zn, La—Au, Mo—Al, Mo—Ge, Mo—Pd, Nb—Ga, Nb—Sn, Nb—Zn, Ni—In, Ni—Mg, Ni—Zn, Os—Ga, Os—Ge, Os—P, Os—Zn, Pd—Mn, Pt—K, Pt—Na, Pt—Tl, Re—Al, Re—Ga, Re—Ge, Re—Sc, Rh—Bi, Rh—Cd, Rh—In, Rh—Mg, Rh—Mn, Rh—Tl, Ru—Ge, Ru—Mg, Ru—Zn, Sc—Cu, Ta—Al, Ta—Fe, Ta—Sn, Ta—Zn, Tc—Ge, Tc—V, Tc—Zn, Ti—Cd, Ti—In, V—Ga, W—Al, W—Ge, W—Hf, W—Ir, W—Pt, W—Zr, Zr—Ag, and Zr—Cu.

Comparative Example 1

Nanocrystalline Stability Map for a Positive Heat of Mixing Alloy System

Which of the situations discussed above is relevant for a given alloy system depends principally upon its mixing parameters (in the grains and intergranular region). Through the thousands of individual calculations conducted, we were able to delineate regimes in the mixing-parameter space corresponding to each behavior described above. These regions of stability are plotted (FIG. 15), using as axes the enthalpies of mixing (Eq. 6) and segregation (Eq. 11).

It was found that the regions separating stability, metastability, or unsuitability of a nanostructured alloy system with a positive enthalpy of mixing are demarcated by straight lines in the double-logarithmic space of FIG. 15. While these lines are not of slope unity, they correspond to a power-law, and can be empirically captured by Eq. (12):

$$\frac{\Delta H_{seg}}{\Delta H_{mix}^a} = c,$$

where a is the power-law slope, and c reflects the intercepts. Both of these are in general a function of temperature; for the map presented in FIG. 15, T=0.35 $T_{cr}$. They may be obtained by fitting a certain number of data points. For other temperatures investigated thus far (see Table 1), the map has the same basic form, but with shifted boundaries reflected in the different fitted values of a and c.

TABLE 1

Coefficients for the Nanostructuring figure of merit, Eq. (12) at three temperatures, as a function of the critical temperature

| Temperature | a (slope) | c (intercepts) | |
|---|---|---|---|
| | | Metastable | Stable |
| 0.35 $T_{cr}$ | 0.757 | 1.7326 | 2.768 |
| 0.5 $T_{cr}$ | 0.661 | 2.8038 | 3.7236 |
| 0.65 $T_{cr}$ | 0.567 | 4.425 | 4.958 |

At the highest level, the map in FIG. 15 shows the trade-off between grain boundary and bulk segregation tendencies as controlling the ability to stabilize a nanocrystalline phase. In fact, the power-law-modified ratio of the two quantities collected on the left-hand side of Eq. (12), $\Delta H_{seg}/\Delta H_{mix}^a$, represents a useful figure of merit for binary systems' nanostructuring ability, with higher values lying more towards the upper-left of the stability map.

Comparative Example 2

Construction of Nanocrystalline Stability Map for a Positive Heat of Mixing Alloy System The boundary of the stable phase region on the map for a nanocrystalline alloy may be determined by the relationship:

$$\frac{\Delta H_{seg}}{\Delta H_{mix}^a} = c, \quad (12)$$

wherein $\Delta H_{mix}$ and $\Delta H_{seg}$ each independently represents an enthalpy of mixing and an enthalpy of segregation (or "segregation enthalpy") of a particular alloy system; a and c are temperature dependent constants and each independently represents a slope and an intercept of each of the boundary lines.

The enthalpy of mixing used in the RNS calculations is that of a regular binary solution, $$\Delta H_{mix} = z\omega_g X(1-X), \quad (13)$$

where z is the coordination number and ω is the interaction parameter describing the tendency of atoms to phase separate or order, based on the energies associated with like and unlike atomic bonds:

$$\omega = E^{AB} - \frac{E^{AA} + E^{BB}}{2}, \quad (14)$$

wherein the subscript g on the interaction parameter in the enthalpy of mixing denotes that the interactions described are those in the grain interior (or if the material were single crystalline, the bulk). Eq. (14) is the same as Eq. (5) above. The segregation enthalpy for this work is an interplay between the interactions in the grain interior and those of the grain boundary, or intergranular (ig) region:

$$\Delta H_{seg}^0 = z\left(\omega_g - \frac{\omega_{ig}}{2}\right). \quad (15)$$

In one embodiment, Equation (15) arises from the assumption of equal grain boundary energies/atomic volume combination, Ωγ/t for solute and solvent content when constructing the stability map and associated figure of merit.

Enthalpy of Mixing

There are many ways to calculate the enthalpy of mixing for a wide range of alloys for the construction of the stability map. For example, one may use thermodynamic analytical models, ab initio computer simulations, atomistic computer simulations, thermodynamic software, phase diagram information, direct experimental measurements by, e.g., calorimetry, grain boundary chemical analysis, etc.; any of these methods may be used in connection with the present inventions. For example, an analytical model like the Miedema model may be employed for the determination of the enthalpy of formation of a concentrated (i.e. not dilute) solid solution:

$$\Delta H_{s.s.}^{form} = \Delta H_{s.s.}^{chemical} + \Delta H_{s.s.}^{elastic} + \Delta H_{s.s.}^{structural}. \quad (16)$$

The expression contains three terms that describe the chemical, elastic, and structural enthalpy changes associated with a solid solution of two atomic species. The structural term was found by Miedema and others to be negligible (±1 kJ/mol, and only if both species are transition metals), therefore we omit this term in our calculations. The contributions to the chemical and elastic terms are summarized in Table 2.

TABLE 2

Miedema Enthalpy of Mixing Terms

| | | | |
|---|---|---|---|
| $V_A, V_B$ | molar volume | $\psi_A, \psi_B$ | work function for electron transfer |
| $c_A, c_B$ | concentration | $n_{ws}^A, n_{ws}^B$ | electron density at boundary of Wigner- |
| $c_A^s, c_B^s$ | surface fraction | | Seitz cell |
| K | bulk modulus | P, Q | Constants |
| G | shear modulus | $W_A, W_B$ | spherical volume of an atom or hole |

$$\Delta H_{s.s.}^{chemical} = c_A c_B (c_B^s \Delta H_{AinB}^{inter} + c_A^s \Delta H_{BinA}^{inter})$$

$$\Delta H_{AinB}^{inter} = \frac{(V_A)^{2/3}}{\frac{1}{2}\left(\frac{1}{n_{ws}^{A1/3}} + \frac{1}{n_{ws}^{B1/3}}\right)}\left\{-P(\Delta\psi)^2 + Q\left(\Delta n_{ws}^{\frac{1}{3}}\right)^2\right\} \quad \Delta H_{BinA}^{inter} = \frac{(V_B)^{2/3}}{\frac{1}{2}\left(\frac{1}{n_{ws}^{A1/3}} + \frac{1}{n_{ws}^{B1/3}}\right)}\left\{-P(\Delta\psi)^2 + Q\left(\Delta n_{ws}^{\frac{1}{3}}\right)^2\right\}$$

$$c_A^s = \frac{c_A * V_A^{2/3}}{c_A * V_A^{2/3} + c_B * V_B^{2/3}} \qquad c_B^s = \frac{c_B * V_B^{2/3}}{c_A * V_A^{2/3} + c_B * V_B^{2/3}}$$

$$\Delta H_{s.s.}^{elastic} = c_A c_B (c_B \Delta H_{AinB}^{elastic} + c_A \Delta H_{BinA}^{elastic})$$

$$\Delta H_{AinB}^{elastic} = \frac{2 * K_A * G_B * (W_A - W_B)^2}{3 * K_A * W_B + 4 * G_B * W_A} \qquad \Delta H_{BinA}^{elastic} = \frac{2 * K_B * G_A * (W_A - W_B)^2}{3 * K_B * W_A + 4 * G_A * W_B}$$

$$W_A = \left(V_A + \alpha * \frac{(\psi_A - \psi_B)}{n_{ws}^A}\right) \qquad W_B = \left(V_B + \alpha * \frac{(\psi_A - \psi_B)}{n_{ws}^B}\right)$$

$$\alpha = 1.5 * \frac{(V_A)^{2/3}}{\frac{1}{n_{ws}^{A1/3}} + \frac{1}{n_{ws}^{B1/3}}} \qquad \alpha = 1.5 * \frac{(V_B)^{2/3}}{\frac{1}{n_{ws}^{A1/3}} + \frac{1}{n_{ws}^{B1/3}}}$$

The chemical term includes $\Delta H_{AinB}^{inter}$, which describes the chemical interaction of an A atom completely surrounded by B atoms and the surface fraction, $c_A^s$, which describes the adjustment made when the A atom has non-B neighbors. The elastic term makes use of Eshelby's elastic formalism and describes fitting an approximate sphere of one atom in a hole in the matrix of the other species.

The Miedema enthalpy is not in the form of a regular solution; in order to extract the regular solution interaction parameter ($\Omega = z\omega$), $\Delta H_{s.s.}^{form}$ was calculated across the full range of X and fit to an equation of the form $\Omega X(1-X)$.

While the Miedema model makes a reasonable estimate for a wide range of binary alloys, it can sometimes result in non-physical predictions; for example, the calculated formation enthalpy is negative (indicating an ordering system) while the phase diagram presents a phase-separating miscibility gap.

The next source for a wide range of alloys is the CAL-PHAD method of calculating phase diagrams. Most free energy functions fitted using this method utilize the Redlich-Kister-Muggiano equation for the excess free energy term (enthalpy of mixing):

$$G^{excess} = X_A X_B \Sigma_i (X_A - X_B)^i L_i(T) \text{ where } L_i(T) = A_i + B_i T$$

The full form for the excess term is fit to the regular solution to find the interaction parameter, $\Omega = z\omega$. For RKM coefficients that are temperature dependent, the particular multiple of the critical temperature (describing the top of the miscibility gap in a phase-separating system, $T_{cr} = z\omega_g/2R$) being used for the figure of merit constants a and c is used in the calculation; for example T is replaced with $0.35*\Omega/2R$ in the RKM coefficient when calculating the figure of merit for $0.35*T_{cr}$.

Finally, interatomic potentials for atomistic modeling of binary alloys (e.g. EAM) can be used for the enthalpy of mixing. Often reported is the dilute mixing enthalpy, the enthalpy associated with one atom of species A, surrounded by atoms of species B. This type of term is analogous to Miedema's $\Delta H_{AinB}^{inter}$; as such, to calculate an enthalpy of mixing for a non-dilute solid solution, it is used in place of s $\Delta H_{AinB}^{inter}$ (Table 2) in the chemical term of Eq. (16).

Enthalpy of Segregation

Interfacial segregation is often characterized via the following isotherm relating the composition of the interface, $x_i$, the composition of the bulk, X, and the segregation enthalpy, $\Delta H_{seg}$:

$$\frac{x_i}{1-x_i} = \frac{X}{1-X}\exp\left[-\frac{\Delta H_{seg}}{RT}\right]. \quad (17)$$

The $\Delta H_{seg}$ describes the change in enthalpy associated with exchanging an atom of one species from the bulk with an atom of another species at the interface (the segregating atom is not required to be the minority/solute element). There are three contributions in existing models for the segregation: elastic (the strain energy associated with mis-fitting atoms), chemical (the interaction energy between the two species of atoms), and interfacial energy (the difference in surface/grain boundary energies of the two species).

The elastic strain energy change can be written using "continuum linear elastic formalism":

$$\Delta E_{el} = \frac{24\pi K_A G_B r_B r_A (r_B - r_A)^2}{3K_A r_A + 4G_B r_B} \quad (18)$$

Solute is denoted by subscript B and solvent by subscript A; K is bulk modulus, G is shear modulus, r is the atomic radius. This term is positive, meaning the elastic component always favors segregation.

The difference in interfacial energies, $\gamma$, and the area per mole of the interface, $\sigma = N_{avg} V_B^{2/3}$ is described by the first term of Eq. (19):

$$\Delta E_{chem} = (\gamma_B - \gamma_A)\sigma + 2\omega[z^l(x - x^s) + z^v(x - \tfrac{1}{2})]; \quad (19)$$

while the second term describes the chemical interactions; where $\omega$ is the interatomic interaction parameter, the total coordination number of the system, z, is split into in-plane, $z^l$, and out of plane, $z^v$, coordination through the following relation: $z = z^l + 2z^v$. The combination of Eq. (18) and Eq. (19) is the Wynblatt-Ku model for interfacial segregation.

These terms were first used to model surface segregation; it has been shown that the elastic term needs no modification to be used in both surface segregation and grain boundary. Darling and coworkers suggest modifications to the Wynblatt-Ku model for use with grain boundaries:

$$\Delta H_{seg} = (\gamma_B - \gamma_A)(1-\alpha)\sigma - \frac{8\Delta H_{mix}}{z}\left[z^l(x^s - x) - z^v\left[\left(x - \tfrac{1}{2}\right) + \alpha\left(x^s - \tfrac{1}{2}\right)\right]\right] - \Delta E_{el}. \quad (20)$$

The interfacial energy term is modified by a parameter, $\alpha$, which accounts for the ratio between interfacial and surface strengths (arbitrarily chosen in their work as 5/6).

In order to solve for the segregation state, Equation (17) is solved with the model for segregation energy (i.e. Wynblatt-Ku or Eq. (20)). The value of the segregation enthalpy cannot be calculated independently of the composition profile, temperature, or other variables. To make an estimation of the segregation energy separately, without a need for solving equation (17) or making any concentration assumptions, Miedema's model was used for surface segregation calculation:

$$\Delta H_{seg} = 0.71 * \tfrac{1}{3} * [-\Delta H_{AinB}^{int} - c_0 \gamma_B V_B^{2/3} + c_0 \gamma_A V_A^{2/3}]. \quad (21)$$

The chemical interaction term, $H_{AinB}^{int}$, $\gamma$, and V are defined the same as above; the term $$c_0 \gamma V^{\tfrac{2}{3}},$$

is the surface enthalpy of a pure metal as defined by Miedema, and $c_0$ is a semi-empirical constant defined as $4.5 \times 10^8$.

The coefficient ⅓ describes the fraction of contact at a surface—when the A atom is at the surface rather than the bulk, it has gone from being surrounded by B atoms to having only ⅔ in contact. With this fractional contact, ⅓ of the interfacial energy is lost (⅓$\Delta H_{AinB}^{int}$), ⅓ of the surface that was B is lost, and ⅓ of the surface is now A. The coefficient 0.71 is due to surface relaxation (both of the surface electron density distribution and the geometry of the surface layer). As a result, the fraction of the surface area of a surface layer atom in contact with the vacuum gets smaller than ⅓.

In Eq. (21) both chemical interaction energy, $\Delta H_{AinB}^{int}$, and interfacial energy terms describing the chemical and interfacial driving forces for segregation are mirrored in the previously discussed models for segregation. From the RNS model, v, the fraction of interface atoms contributing to the effective coordination of transitional bonds, is taken to be ½. Following the Miedema formulation, an atom in the grain boundary will lose one sixth of its contact with other atoms.

Elastic term, Eq. (18), was added to account for the elastic strain effects that contribute to segregation:

$$\Delta H_{seg} = 0.71 * \tfrac{1}{6} * \left[-\Delta H_{AinB}^{int} - \frac{c_0}{f}\gamma_B V_B^{\tfrac{2}{3}} + \frac{c_0}{f}\gamma_A V_A^{\tfrac{2}{3}}\right] - \Delta E_{el} \quad (22)$$

Equation (22) has no temperature and composition assumptions and contains readily available materials data.

Resultant stability maps in some embodiments are provided in FIGS. 15-18B. As further described below, over 100 alloy compositions have been evaluated using the stability map provided herein. FIGS. 16-18B further separate the types of alloys shown on a stability map into FCC, HCP, and BCC, respectively; each of FIGS. 16-18B are constructed to illustrate stability behavior of binary alloys at a temperature of 0.35 $T_{cr}$. Green region: stable NC microstructure; yellow region: metastable NC microstructure; red region: no stable NC microstructure. Base alloy metal is described by the symbol and solute alloy is indicated by the accompanying matching color label. Alloys estimated with a model other than Miedema's are indicated with a red outline of the symbol.

Based on the calculations performed herein, including the results shown in FIGS. 16-18B, it was determined that a number of binary alloys with a positive heat of mixing may exist in a stable nanocrystalline phase against grain growth and phase separation—e.g., the alloy systems described in P.C.T. Application No. PCT/US2012/028811 designated as exhibiting a stable nanocrystalline phase.

Additional Notes

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." Any ranges cited herein are inclusive.

The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed:

1. An alloy comprising:
a mixture of a solute element and a solvent element, the mixture having a phase including at least one of a stable nanocrystalline phase, a metastable nanocrystalline phase, and a non-nanocrystalline phase,
the phase having a first thermodynamic parameter associated with grain boundary segregation of the alloy system, a second thermodynamic parameter associated with phase separation of the alloy system, and a third thermodynamic parameter associated with intermetallic compound formation of the alloy system,
wherein the phase is stable when the first thermodynamic parameter, the second thermodynamic parameter, and the third thermodynamic parameter are within a predetermined region of a stability map of the alloy.

2. The alloy of claim 1, wherein an enthalpy of mixing is negative.

3. The alloy of claim 1, wherein the alloy includes an intermetallic compound.

4. The alloy of claim 1, wherein the alloy is an ordered binary alloy comprising at least one of Ag—Sc, Ag—La, Ag—Y, Ba—Pd, Ba—Pt, Be—Ti, Bi—Pd, Ca—Pt, Cd—Pd, Co—Al, Co—As, Co—Ga, Co—Ge, Co—Hf, Co—Nb, Co—Sc, Co—Ta, Co—Ti, Co—Y, Co—Zr, Cr—Pt, Cu—Sc, Fe—Al, Fe—As, Fe—Hf, Fe—Sc, Fe—Zr, Hf—Ag, Hf—Bi, Hf—Co, Hf—Ni, Hf—Os, Hf—Re, Hf—Tl, Ir—Cd, Ir—Cr, Ir—Ge, Ir—In, Ir—Mg, Ir—Mn, Ir—Sb, Ir—Zn, La—Ag, La—Au, La—Ir, La—Rh, La—Zn, Mn—Ga, Mn—Pd, Mn—Sb, Mo—Al, Mo—Ge, Mo—Pd, Nb—Co, Nb—Ga, Nb—Ni, Nb—Re, Nb—Sb, Nb—Sn, Nb—Zn, Ni—Ga, Ni—Ge, Ni—Hf, Ni—In, Ni—La, Ni—Mg, Ni—Nb, Ni—Ta, Ni—Th, Ni—Y, Ni—Zn, Os—As, Os—Ga, Os—Ge, Os—P, Os—V, Os—Y, Os—Zn, Pd—Mn, Pt—Bi, Pt—K, Pt—Mn, Pt—Na, Pt—Tl, Re—Al, Re—As, Re—Ga, Re—Ge, Re—Hf, Re—Nb, Re—Sc, Re—Ta, Re—Ti, Rh—Bi, Rh—Cd, Rh—In, Rh—Mg, Rh—Mn, Rh—Sb, Rh—Sn, Rh—Tl, Rh—Zn, Ru—Ga, Ru—Ge, Ru—La, Ru—Mg, Ru—V, Ru—Y, Ru—Zn, Sc—Ag, Sc—Cu, Sc—Ni, Sc—Os, Sc—Ru, Sc—Tc, Sn—Pd, Sr—Pd, Sr—Pt, Ta—Al, Ta—Fe, Ta—Ga, Ta—Ni, Ta—Re, Ta—Sb, Ta—Sn, Ta—Zn, Tc—Ge, Tc—La, Tc—Th, Tc—V, Tc—Y, Tc—Zn, Th—Ir, Th—Rh, Ti—Be, Ti—Bi, Ti—Cd, Ti—Co, Ti—In, Ti—Ni, Ti—Pb, Ti—Sn, Ti—Zn, V—Ga, V—Ru, V—Sb, V—Tc, W—Al, W—As, W—Ge, W—Hf, W—Ir, W—Pt, W—Si, W—Zr, Y—Ag, Y—Ir, Y—Rh, Y—Zn, Zn—Hf, Zn—La, Zn—Sc, Zn—Y, Zr—Ag, Zr—Be, Zr—Co, Zr—Cu, and Zr—Ni.

5. The alloy of claim 1, wherein the alloy is a nanocrystalline alloy having an average grain size of less than about 1,000 nm.

6. The alloy of claim 1, wherein the alloy is substantially thermodynamically stable at a temperature of 1,000 K.

7. The alloy of claim 1, wherein the alloy is substantially free of a classical segregation-stabilized nanocrystalline phase.

8. The alloy of claim 1, wherein the alloy is formed using at least one of electrodeposition, physical vapor deposition, chemical vapor deposition, plasma-spraying, mechanical alloying, casting, and solidification.

9. The alloy of claim 1, wherein the alloy is mechanically alloyed.

10. An alloy comprising:
a mixture of a solute element and a solvent element,
the mixture having a phase including at least one of a stable nanocrystalline phase, a metastable nanocrystalline phase, and a non-nanocrystalline phase,
the phase being stable when a plurality of thermodynamic parameters are within a predetermined region of a stability map of the alloy, and
the alloy comprising grains having a largest dimension smaller than about 1,000 nm.

11. The alloy of claim 10, wherein the alloy is an ordered binary alloy comprising at least one of Ag—Sc, Ag—La, Ag—Y, Ba—Pd, Ba—Pt, Be—Ti, Bi—Pd, Ca—Pt, Cd—Pd, Co—Al, Co—As, Co—Ga, Co—Ge, Co—Hf, Co—Nb, Co—Sc, Co—Ta, Co—Ti, Co—Y, Co—Zr, Cr—Pt, Cu—Sc, Fe—Al, Fe—As, Fe—Hf, Fe—Sc, Fe—Zr, Hf—Ag, Hf—Bi, Hf—Co, Hf—Ni, Hf—Os Hf—Re, Hf—Tl, Ir—Cd, Ir—Cr, Ir—Ge, Ir—In, Ir—Mg, Ir—Mn, Ir—Sb, Ir—Zn, La—Ag, La—Au, La—Ir, La—Rh, La—Zn, Mn—Ga, Mn—Pd, Mn—Sb, Mo—Al, Mo—Ge, Mo—Pd, Nb—Co, Nb—Ga, Nb—Ni, Nb—Re, Nb—Sb, Nb—Sn, Nb—Zn, Ni—Ga, Ni—Ge, Ni—Hf, Ni—In, Ni—La, Ni—Mg, Ni—Nb, Ni—Ta, Ni—Th, Ni—Y, Ni—Zn, Os—As, Os—Ga, Os—Ge, Os—P, Os—V, Os—Y, Os—Zn, Pd—Mn, Pt—Bi, Pt—K, Pt—Mn, Pt—Na, Pt—Tl, Re—Al, Re—As, Re—Ga, Re—Ge, Re—Hf, Re—Nb, Re—Sc, Re—Ta, Re—Ti, Rh—Bi, Rh—Cd, Rh—In, Rh—Mg, Rh—Mn, Rh—Sb, Rh—Sn, Rh—Tl, Rh—Zn, Ru—Ga, Ru—Ge, Ru—La, Ru—Mg, Ru—V, Ru—Y, Ru—Zn, Sc—Ag, Sc—Cu, Sc—Ni, Sc—Os, Sc—Ru, Sc—Tc, Sn—Pd, Sr—Pd, Sr—Pt, Ta—Al, Ta—Fe, Ta—Ga, Ta—Ni, Ta—Re, Ta—Sb, Ta—Sn, Ta—Zn, Tc—Ge, Tc—La, Tc—Th, Tc—V, Tc—Y, Tc—Zn, Th—Ir, Th—Rh, Ti—Be, Ti—Bi, Ti—Cd, Ti—Co, Ti—In, Ti—Ni, Ti—Pb, Ti—Sn, Ti—Zn, V—Ga, V—Ru, V—Sb, V—Tc, W—Al, W—As, W—Ge, W—Hf, W—Ir, W—Pt, W—Si, W—Zr, Y—Ag, Y—Ir, Y—Rh, Y—Zn, Zn—Hf, Zn—La, Zn—Sc, Zn—Y, Zr—Ag, Zr—Be, Zr—Co, Zr—Cu, and Zr—Ni.

12. The alloy of claim 10, wherein the plurality of thermodynamic parameters are associated with at least two of grain boundary segregation, phase separation of the alloy system, and intermetallic compound formation of the alloy system.

13. The alloy of claim 10, wherein the alloy is substantially thermodynamically stable at a temperature of 1,000 K.

14. The alloy of claim 10, wherein the alloy is substantially free of a classical segregation-stabilized nanocrystalline phase.

15. The alloy of claim 10, wherein the alloy is formed by at least one of electrodeposition, physical vapor deposition, chemical vapor deposition, plasma-spraying, mechanical alloying, casting, and solidification.

* * * * *